(12) United States Patent
Botvinick et al.

(10) Patent No.: US 10,156,561 B2
(45) Date of Patent: Dec. 18, 2018

(54) MECHANICAL STRESS RESPONSE ANALYSIS OF CELLS AND TISSUES

(71) Applicant: The Regents of The University of California, Oakland, CA (US)

(72) Inventors: Elliot L. Botvinick, Irvine, CA (US); Vasan Venugopalan, Irvine, CA (US); Jonathan Compton, Irvine, CA (US); Amy Hellman, Huntington Beach, CA (US)

(73) Assignee: The Regents of The University of California, Oakland, CA (US)

( * ) Notice: Subject to any disclaimer, the term of this patent is extended or adjusted under 35 U.S.C. 154(b) by 52 days.

(21) Appl. No.: 15/253,650

(22) Filed: Aug. 31, 2016

(65) Prior Publication Data

US 2017/0059557 A1    Mar. 2, 2017

Related U.S. Application Data

(62) Division of application No. 14/046,804, filed on Oct. 4, 2013, now abandoned.

(60) Provisional application No. 61/710,602, filed on Oct. 5, 2012.

(51) Int. Cl.
*G01N 33/50*   (2006.01)
*C40B 30/06*   (2006.01)
*G01N 33/543*  (2006.01)

(52) U.S. Cl.
CPC ..... *G01N 33/5032* (2013.01); *G01N 33/5064* (2013.01); *G01N 33/54373* (2013.01); *C40B 30/06* (2013.01)

(58) Field of Classification Search
None
See application file for complete search history.

(56) References Cited

U.S. PATENT DOCUMENTS

| 6,534,308 | B1 | 3/2003 | Palsson et al. |
| 7,092,557 | B2 | 8/2006 | Eisfeld et al. |
| 7,300,795 | B2 | 11/2007 | Koller et al. |
| 2010/0041128 | A1 | 2/2010 | Banes et al. |

FOREIGN PATENT DOCUMENTS

| WO | WO 2007103135 | 9/2007 |
| WO | WO 2011011644 | 1/2011 |

OTHER PUBLICATIONS

Hellman, "Pulsed laser microbeams for cellular manipulation: applications in cell biology and microfluidics," Ph.D. dissertation, University of California, San Diego, 2008.*

(Continued)

*Primary Examiner* — Kaijiang Zhang
(74) *Attorney, Agent, or Firm* — Nguyen & Tarbet Law Firm

(57) ABSTRACT

A method and device are disclosed for inducing mechanical stress in a cellular sample to evaluate mechanotransduction in the cellular sample. In one embodiment, the mechanical stress is induced by generating a microcavitation bubble in the cellular sample using a pulsed energy. The microcavitation bubble creates a microtsunami, which provides a transient, impulsive mechanical stress on the cellular sample, forming a gradient of effects at distances away from the microcavitation bubble.

10 Claims, 18 Drawing Sheets

(56) References Cited

OTHER PUBLICATIONS

Wang et al., "Visualizing the mechanical activation of Src," Nature 2005, 434:1040-1045.*
Wang, Y., et al., Visualizing the mechanical activation of Src, Nature 434, 1040-45 (2005).
Peyton, S.R., et al., The use of poly(ethyleneglycol) hydrogels to investigate the impact of ECM chemistry and mechanics on smooth muscle cells, Biomaterials 27, 4881-93 (2006).
Kumar, S., et al., Viscoelastic retraction of single living stress fibers and its impact on cell shape, cytoskeletal organization, and extracellular matrix mechanics, Biophysical Journal 90, 3762-79 (2006).
Discher, D.E., et al., Tissue cells feel and respond to the stiffness of their substrate, Science 10, 1139-43 (2005).
Ingber, D.E., Tensegrity: the architectural basis of cellular mechanotransduction, Annual Review of Physiology 59, 575-99 (1997).
Jaalouk, D.E. & Lammerding, J., Mechanotransduction gone awry, Nature Reviews Molecular Cell Biology 10, 63-73 (2009).
Oerr, A.W., et al., Mechanisms of mechanotransduction, Developmental Cell 10, 11-20 (2006).
Ingber, D., Mechanobiology and diseases of mechanotransduction, Annals of Medicine 35, 564-577 (2003).
Hahn, C. & Schwartz, M.A., Mechanotransduction in vascular physiology and atherogenesis. Nature Reviews Molecular Cell Biology 10, 53-62 (2009).
Gottlieb, P.A., et al., Mechanosensitive ion channels as drug targets, Current Drug Targets CNS and Neurological Disorders 3, 287-95 (2004).
Huh, D., et al., From 3D cell culture to organs-on-chips, Trends in Cell Biology 21, 745-54 (2011).
Apic, G., et al., Illuminating drug discovery with biological pathways, FEBS Letters 579, 1872-7 (2005).
Drews, J., Drug Discovery: A Historical Perspective, Science 287, 1960-1964 (2000).
Rudin, M. & Weissleder, R., Molecular imaging in drug discovery and development, Nature Reviews Drug Discovery 2, 123-31 (2003).
Charras, G.T. & Horton, M.A., Single cell mechanotransduction and its modulation analyzed by atomic force microscope indentation, Biophysical Journal 82, 2970-81 (2002).
Chien, S., Effects of disturbed flow on endothelial cells, Annals of Biomedical Engineering 36, 554-62 (2008).
Valberg, P.A. & Butler, J.P., Magnetic particle motions within living cells. Physical theory and techniques, Biophysical Journal 52, 537-50 (1987).
Chen, C.S., et al., Geometric control of cell life and death, Science 276, 1425-8 (1997).
Rau, KR., et al., Pulsed laser microbeaminduced cell lysis: time-resolved imaging and analysis of hydrodynamic effects, Biophysical Journal 91, 317-29 (2006).
Hellman, A.N., et al., Biophysical response to pulsed laser microbeam-induced cell lysis and molecular delivery, Journal of Biophotonics 1, 24-35 (2008).
Vogel, A. & Venugopalan, V., Mechanisms of pulsed laser ablation of biological tissues, Chemical Reviews 103, 577-644 (2003).
Vogel, A., et al., Mechanisms of femtosecond laser nanosurgery of cells and tissues. Applied Physics B 81. 1015-1047 (2005).
Venugopalan, V., et al., Role of Laser-Induced Plasma Formation in Pulsed Cellular Microsurgery and Micromanipulation Physical Review Letters 88, 1-4 (2002).
Vogel, A., Nonlinear absorption: intraocular microsurgery and laser lithotripsy, Physics in Medicine and Biology 42, 895-912 (1997).
Stevenson, D.J., et al., Single cell optical transfection, Journal of the Royal Society, Interface 7, 863-71 (2010).
Gilmore, F.R., The Growth or Collapse of a Spherical Bubble in a Viscous Liquid. Office of Naval Research (1952).
Knapp, R.T., et al., Cavitation, (McGraw-Hill: New York, 1970).
Vogel, A., et al., Shock wave emission and cavitation bubble generation by picosecond and nanosecond optical breakdown in water, The Journal of the Acoustical Society of America 100, 148 (1996).
Vogel, A., et al., Femtosecond-Laser-Induced Nanocavitation in Water: Implications for Optical Breakdown Threshold and Cell Surgery, Physical Review Letters 100, 1-4 (2008).
Lokhandwalla, M. & Strutevant, B., Mechanical haemolysis in shock wave lithotripsy (SWL): I. Analysis of cell deformation due to SWL flow-fields, Physics in Medicine and Biology 46, 413-37 (2001).
Malek, A.M., et al., Hemodynamic shear stress and its role in atherosclerosis, JAMA; The Journal of the American Medical Association 282, 2035-42 (1999).
Davies. P.F., Flow-mediated endothelial mechanotransduction, Physiological Reviews 75, 519-60 (1995).
Tran, Q. K. & Watanabe, H., Calcium signalling in the endothelium, Handbook of Experimental Pharmacology 2, 145-87 (2006).
Kuchan, M.J. & Frangos, J. A., Role of calcium and calmodulin in flow-induced nitric oxide production in endothelial cells, The American Journal of Physiology 266, C628-36 (1994).
Okuda, M., et al., Shear stress stimulation of p130(cas) tyrosine phosphorylation requires calcium dependent c-Src activation, The Journal of Biological Chemistry 274, 26803-9 (1999).
Chien, S., Mechanotransduction and endothelial cell homeostasis: the wisdom of the cell, American Journal of Physiology Heart and Circulatory Physiology 292, H1209-24 (2007).
Palmer, A.E. & Tsien, R.Y., Measuring calcium signaling using genetically targetable fluorescent indicators, Nature Protocols 1, 1057-65 (2006).
Bishara, N.B., et al., Capacitative Ca(2+) entry in vascular endothelial cells is mediated via pathways sensitive to 2 aminoethoxydiphenyl borate and xestospongin C, British Journal of Pharmacology 135, 119-28 (2002).
Demer, L.L., et al., Mechanical stimulation induces intercellular calcium signaling in bovine aortic endothelial cells, The American Journal of Physiology 264, H2094-102 (1993).
Quinto-Su, P.A., et al., Examination of laser microbeam cell lysis in a PDMS microfluidic channel using timeresolved imaging, Lab on a Chip 8. 408-14 (2008).
Seong, J., et al., Live Cell Imaging of Src/FAK Signaling by FRET, Cellular and Molecular Bioengineering 4, 138-147 (2011).
Cherian, A.V. & Rau, K.R., Pulsed-laser-induced damage in rat corneas: time-resolved imaging of effects and acute biological response, Journal of Biomedical Optics 13, 024009 (2008).
Shergill, B., et al., Optical tweezers studies on notch single-molecule interaction strength is independent of ligand endocytosis, Developmental Cell 22, 1313-20 (2012).
Meloty-Kapella, L., et al., Ligand endocytosis generates mechanical pulling force dependent on dynamin, epsins, and actin, Developmental Cell 22, 1299-312 (2012).
Neuzil, P., et al., Revisiting lab-on-a-chip technology for drug discovery. Nature Reviews Drug Discovery 11, 620-32 (2012).
Young, E.W.K. & Simmons, C.A., Macro- and microscale fluid flow systems for endothelial cell biology, Lab on a Chip 10, 143-60 (2010).
Blackmon, B.R., et al., A new in vitro model to evaluate differential responses of endothelial cells to simulated arterial shear stress waveforms, Journal of Biomechanical Engineering 124, 397-407 (2002).
Stuurman, N., et al., Computer control of microscopes using μManager, Current Protocols in Molecular Biology, edited by Frederick M. Ausubel et al, Chapter 14, Unit14.20 (2010).
Park, J.W., et al., Microfluidic culture platform for neuroscience research, Nature Protocols, vol. 1 No. 4, 2128-2136 (2006).
Yang, M.T., et al., Assaying sem cell mechanobiology on microfabricated elastometric substrates with geometrically modulated rigidity, Nature Protocols, vol. 6 No. 2, 187-213 (2011).
Gulyani, A., et al., A biosensor generated via high throughput screening quantifies cell edge Src dynamics, Nat Chem Biol.; 7(7): 437-444 (2012).
Haug, C., et al., Effect of Diltiazem and Verapamil on Endothelin Release by Cultured Human Coronary Smooth-Muscle Cells and

(56) References Cited

OTHER PUBLICATIONS

Endothelial Cells, Journal of Cardiovascular Pharmacology; vol. 31—Issue pp. S388-3391 (1998).

Vogel, A., et al., Energy balance of optical breakdown in water at nanosecond to femtosecond time scales, Appl. Phys. B 68, 271-280 (1999).

Wang, Y., et al., Selective adapter recruitment and differential signaling networks by VEGF vs. shear stress, PNAS, vol. 104 No. 21 8875-8879 (2007).

Hellman, Pulsed laser microbeams for cellular manipulation: applications in cell biology and microfluids, Ph.D. dissertation, University of California, San Diego, 2008.

Salazar, et al., Micropallet Arrays for the Separation of Single, Adherent Cells, Anal. Chem. 2007, 79:682-687.

* cited by examiner

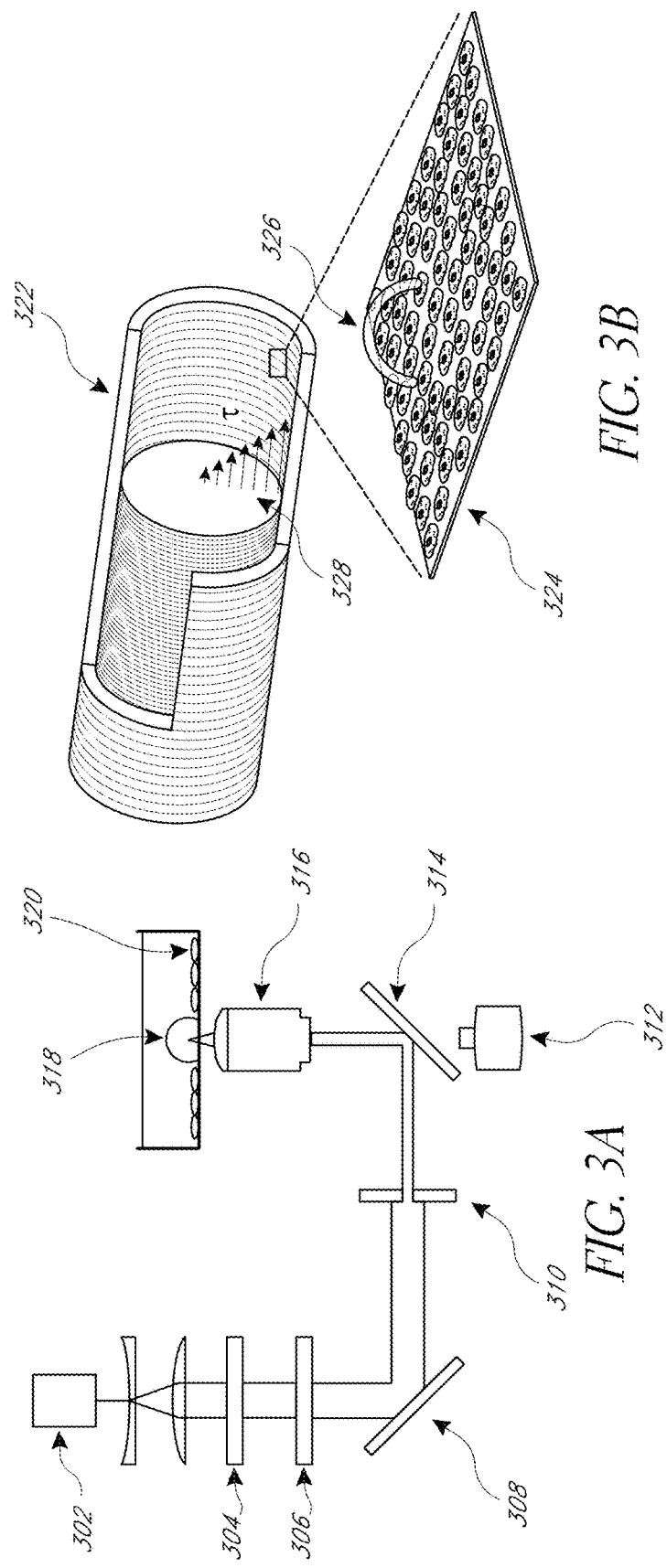

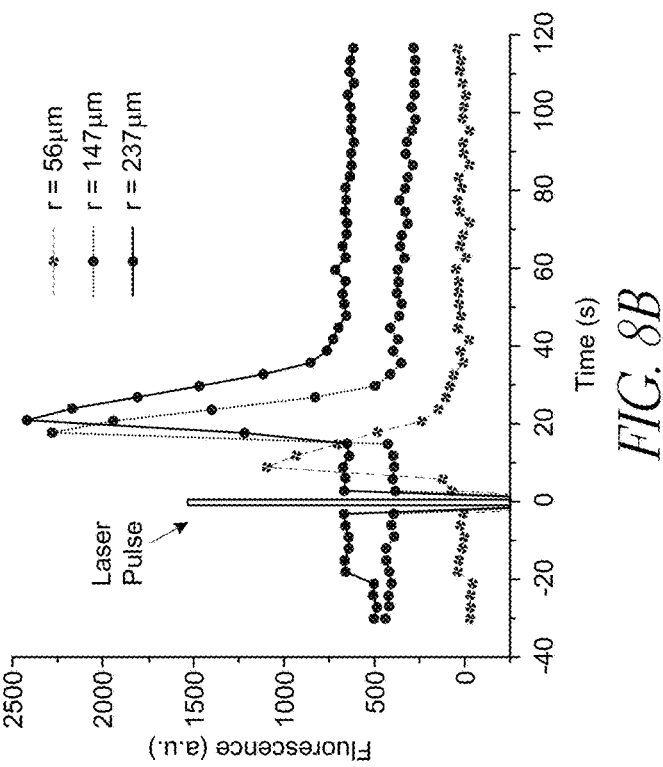
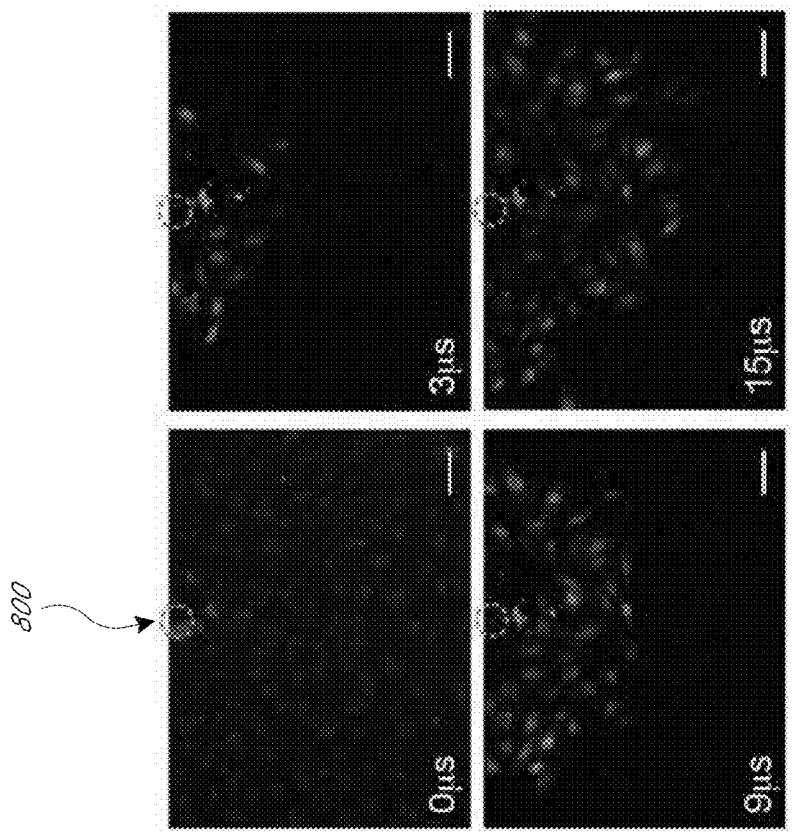
FIG. 8B
FIG. 8A

MECHANICAL STRESS RESPONSE ANALYSIS OF CELLS AND TISSUES

STATEMENT REGARDING FEDERALLY SPONSORED R&D

This research was funded through the Laser Microbeam and Medical Program, a National Biomedical Technology Resource (P41-EB015890) supported by the National Institutes of Health.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

Methods are disclosed for screening mechanical stress responses in cells and tissues using induced cavitation bubbles.

Description of the Related Art

Mechanotransduction, which refers to the mechanical forces resulting from cell-cell and cell-matrix interactions, are known to influence the signaling, function, homeostasis, and fate of individual cells and cell populations. Likewise, numerous studies have demonstrated the important role of mechanotransduction in many vital processes, including, for example: tissue morphogenesis, stem cell differentiation, vascular regulation, and tumor metastasis. Moreover, studies suggest that disruptive mechanical cues and/or dysregulation of physiological mechanotransduction pathways play important roles in the initiation and progression of numerous diseases, including, for example: atrial fibrillation, hypertension, osteoporosis, digestive diseases, and cancer. This has spurred vigorous efforts to discover therapeutic molecules that modulate cellular mechanotransduction activity, which in turn has created the need to develop assays that evaluate the sensitivity of candidate drug targets to mechanosignaling.

Currently, there are several established, high-throughput methods to precisely measure changes in cellular activity, including imaging cytometry and gene arrays. However, precise mechanical stimulation of cells can require specialized techniques such as atomic force microscopy (AFM), optical/magnetic tweezers, dynamically-stretched substrates or laminar flow chambers. While these methods are well-suited for applying physiological forces to cells in two-dimensional (2-D) and three-dimensional (3-D) cell cultures, they are time-intensive and require considerable technical expertise. Some of these methods, including optical tweezers and AFM, have utility in the study of mechanotransduction, but their low throughput means that they can only be used to examine a very limited number of cells per day. Other approaches involve the incubation of cells in specialized microdevices such as laminar flow chambers[16], microfluidic chambers, and micro-fabricated substrates that expose cells to specific physiological mechanical stimuli. While such systems are well-suited to screen a small number of molecules shown to affect mechanotransduction, there is no clear path to scaling up such systems for screening hundreds of thousands of molecules.

As described above, current methods are not standardized and they are not compatible with existing high-throughput drug discovery platforms. Thus, the technical challenge involved in developing a high-throughput platform for applying precise forces to multiple cells in various culture conditions is considerable. The development of such a platform is essential to examining the role of mechanotransduction in important biological processes, and to discovering and characterizing the effects of small molecules that modulate the activity of mechano-sensitive pathways. Therefore, a practical method for the upstream, high-content screening and identification of test compounds is necessary to facilitate the discovery of a class of "mechano-active" drugs that target these "mechano-sensitive" pathways.

SUMMARY OF THE INVENTION

Disclosed herein is a method for discovery and/or screening of test compounds that may modulate cellular mechanotransduction, the method can comprise providing at least one cellular sample, administering a test compound to the at least one cellular sample, initiating a microcavitation bubble at a site within the at least one cellular sample, monitoring a signal related to the cellular mechanotransduction of the at least one cellular sample, and comparing the signal to a control signal, wherein a difference between the signal and the control signal indicates that the candidate test modulates cellular mechanotransduction.

In some embodiments, initiating the microcavitation bubble can comprise applying an energy source to the site. In some embodiments, the energy source is selected from the group consisting of a laser, an ultrasonic transducer, a piezoelectric transducer, or combinations thereof.

In some embodiments, the at least one cellular sample can comprise cells adherent to a two-dimensional substrate. In some embodiments, the at least one cellular sample can comprise a three-dimensional matrix. In some embodiments, the three-dimensional matrix can be selected from the group consisting of a hydrogel, a tissue, a reconstituted tissue, an extracellular matrix, a tissue scaffold or combinations thereof. In some embodiments, the at least one cellular sample can comprise a micro-patterned cellular sample configured to have areas without cells. In some embodiments, the microcavitation bubble can be configured to form a microtsunami.

Disclosed is a method of testing a cellular response to a transient mechanical stimulus, the method can comprise providing a plurality of cellular samples, administering a test compound to at least a first cellular sample, and a control vehicle to at least a second cellular sample, initiating a microtsunami within at least the first and second cellular samples, wherein the test compound and control vehicle may be administered before, during, or after initiating the microtsunami, monitoring a signal related to the cellular response in at least the first and second cellular samples, and comparing the signals from at least the first and second cellular samples, wherein a difference between the signals indicates that the test compound modulates the cellular response to the transient mechanical stimulus.

Disclosed herein is a device for high-throughput discovery and/or screening of test compounds that may modulate cellular mechanotransduction, the device can comprise a holder configured to hold at least one cellular sample, an energy source configured to deliver energy along a path to a site within the at least one cellular sample, wherein the energy is sufficient to generate a microcavitation bubble at the site, and a sensor configured to receive a signal from the at least one cellular sample, wherein the signal is related to cellular mechanotransduction.

In some embodiments, the holder can comprise a movable stage configured to secure a dish comprising one or more wells, each well comprising a cellular sample, an actuator configured to move the movable stage and position each of the one or more wells within the path of the energy, and a controller configured to control the actuator.

In some embodiments, the holder can comprise a stationary stage configured to secure a dish comprising one or more wells, each well comprising a cellular sample, wherein the energy source is configured to move to direct energy to a site in each of the one or more wells.

In some embodiments, the energy source can be selected from a laser, an ultrasonic transducer, a piezoelectric transducer or combinations thereof. In some embodiments, the sensor can comprise a multichannel sensor array configured to receive a more than one signals from the cellular sample.

BRIEF DESCRIPTION OF THE DRAWINGS

FIG. 3A shows an embodiment of a setup for laser-generation of microcavitation bubbles in cell culture.

FIG. 3B is a depiction of hemodynamic shear stress in an arterial vessel model.

FIG. 8A shows a Fluo-3AM time series of cytoplasmic calcium release in HUVECs in response to a single μCB generated microtsunami over a confluent monolayer.

FIG. 8B depicts intracellular calcium-mediated fluorescence dynamics for three cells located at radial positions r=56, 147, and 237 μm from the μCB center. The delay between μCB initiation and calcium signaling increases with distance.

DETAILED DESCRIPTION OF THE PREFERRED EMBODIMENT

Figure 1:
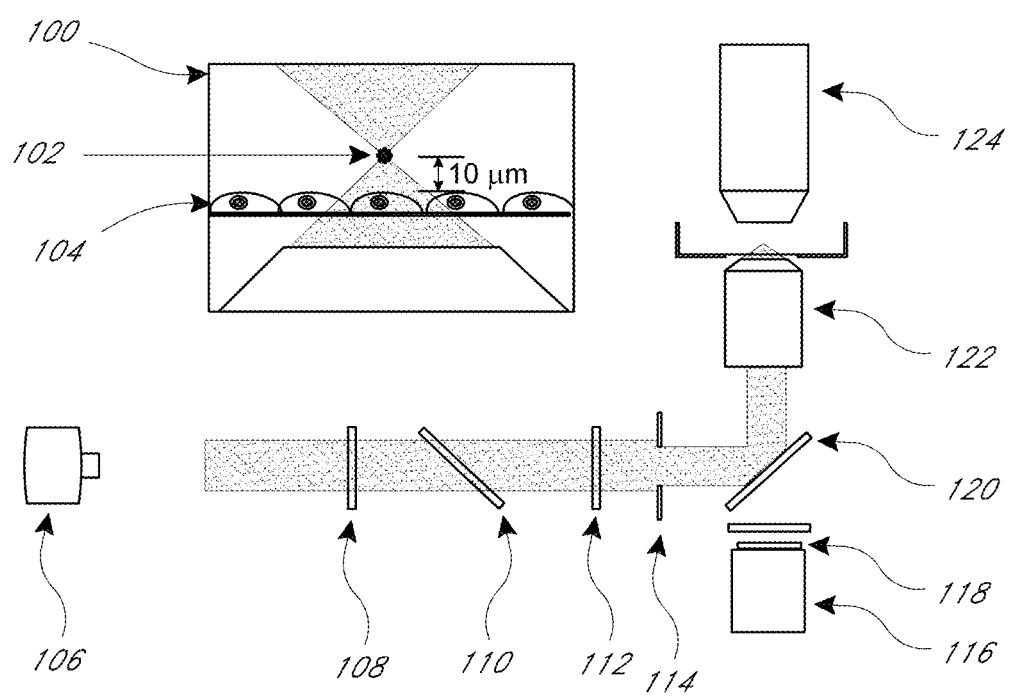
FIG. 1 illustrates an embodiment of a setup for cellular manipulations using laser-generated microcavitation bubbles.

Embodiments of the present disclosure provide for a method of analyzing and/or screening cells and cell cultures using a transient pulse of mechanical stress, and a device for performing such analysis and/or screening. This mechanical stress can lead to mechanotransduction in the cell culture, which can be analyzed. In some embodiments, the mechanotransduction can be compared to an already made library of data for specific cell cultures, or could be compared to control groups that are analyzed by the method at the same time.

Generally, in some embodiments, a high-throughput method can be used for the discovery and screening of test compounds that modulate cellular mechanotransduction pathways. In some embodiments, as described in more detail below, the method can comprise providing a cell culture, administering a test compound to the cell culture, initiating an energy-generated microcavitation bubble (μCB) within the cell culture, and monitoring a signal related to cellular mechanotransduction.

The terms "cells" "cellular sample" and "cell cultures" as used herein are interchangeable and are broad terms that include their ordinary dictionary meaning, and can refer to both in vivo and in vitro cells and cell cultures, as well as any other tissue culture. The types, locations and physical surrounding of the cells are not limiting. For example, human cells, cattle cells, pig cells, and sheep cells can be used, as well as skin, blood, brain, and other tissue. Further, the cell culture is not limited to one type of cell or one location of a cell, and a plurality of different types of cells can be included in the cell culture. In some embodiments, the cells and cell cultures can refer to cells adherent to a substrate in a conventional 2-D monolayer. In other embodiments, the cells and cell cultures can refer to cells within a multi-layered culture, or cells within a 3-D matrix, wherein the matrix may comprise, for example, collagen, elastin, glycosaminoglycans, and any of a variety of known extracellular matrix (ECM) and connective tissue components. In some embodiments, the cell cultures can have micropatterning within the culture. For example, there can be certain areas that are free of cells. These cell free areas can be formed within the cell culture in, for example, rings or lines. The type and amount of micropatterning is not limiting.

Test compounds as used herein are broad terms that include their ordinary dictionary meaning, and can refer to any agent that is being tested for its potential modulation of cellular mechanotransduction. For example, test compounds may include small synthetic molecules, large synthetic molecules, naturally occurring molecules, macromolecules, monomers and polymers, recombinant molecules, etc. The types and relative sizes of the test compounds are not particularly limiting. For example, microRNA, siRNA, microDNA, chimeric nucleic acids, aptamers, antibodies and antibody fragments, light and heavy Ig chains, epitope CDRs, mono, bi and multivalent binding proteins, proteins, peptides, amino acids, carbohydrates, mono and disaccharides, lipids, proteoglycans, growth factors, peptide as well as steroid hormones, cytokines.

The terms "approximately", "about", and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

In some embodiments, the screening method can be performed to, for example, establish the viability of test compound libraries. In some embodiments, the test compound libraries can be screened to identify the compounds that can alter the activity of mechanotransduction pathways in the cells and cell cultures. In some embodiments, the library is already available and the results of the disclosed method can be compared to previous results for the library, determined using other means of inducing mechanical stresses. In some embodiments, a general analysis of the effects of the transient stress pulse can be performed. The method is not limited to any particular use.

Specifically, disclosed below are embodiments of a rapid, high-throughput screening and/or analysis of exogenous molecules or test compounds which may potentially affect cellular mechanotransduction. Using embodiments of the below described method, reliance on flow chambers, bulk flow, and/or microfluidics can be avoided. To do so, the disclosed method can initiate mechanotransduction in cell cultures using μCBs. Many different types of cell cultures such as, for example, primary human vascular endothelial cell (HUVEC) cultures can be used. These μCBs can expose adherent cells to a microtsunami, which is a transient microscale impulse of hydrodynamic shear stress that can stimulate the surrounding cells. The microtsunami can affect cells over areas at least one, two, three, four, or five times greater than the size of the corresponding μCB. The microtsunami can also affect cells that are located within the actual μCB, and the location of the affects cells are not limiting. For example, the μCB may be directed onto a specific cell, and the effect forming the microtsunami within the cell can be studied.

In general, embodiments of the present disclosure comprise a method for screening cells using microcavitation bubbles. In some embodiments, a simple energetic, for example optical, method is provided for the discovery of a class of test compounds that can regulate physiological signaling in response to impulsive mechanical stimuli. Further, the method can be used to analyze the reactions of cells to mechanical stress, regardless of whether any test compounds are being screened.

As discussed in greater detail below, μCBs can be induced in a cell culture, resulting in the initiation of a microtsunami, thereby generating mechanical stresses, or other forces, on the cell culture. These forces can, for example, modulate cellular mechanotransduction pathways, cellular and extracellular signaling, elaboration of autocrine and/or paracrine factors, electrical transduction, etc., near and away from the location of the μCBs. The amplitude of the cellular response to the mechanical stress may be related to the relative mechanical force exerted by the microtsunami. Multiple μCBs can be used in the same culture, at the same time or different times, or a single μCB can be used. The mechanotransduction occurring after the microtsunami can be analyzed and compared with the use of, for example, test compounds, to determine the effectiveness of said test compounds in, for example, affecting the cellular responses to the microtsunami.

In some embodiments, the disclosed method can be used to identify molecules that modulate cellular mechanotransduction, and can be used in conjunction with a drug discovery platform to narrow the number of candidate molecules. This reduced set of molecules can then be investigated further in regards to their downstream cellular effects using existing techniques to expose cells to long-term physiological stresses. In addition to the discovery of "mechano-active" test compounds, the disclosed method can be used to screen for potential adverse off-target effects including, for example, vasoconstrictive or vasodilatory hyperactivity. These downstream effects include but are not limited to, signaling, kinase activity, tyrosine kinase dynamics (e.g. FRET sensors and antibodies), molecular trafficking, cytoskeletal arrangement, cytoplasmic translocation, membrane potential changes, translocation of transcription factors across the nuclear envelope, molecular dynamics (e.g. trafficking, release of molecules from a cellular compartment, active transport, membrane fluidity, for example, the YAP-TAZ pathway in which transcriptional factors are transported into the nucleus downstream of mechanostransduction), mRNA expression (gene expression, genetic networks), chromatin modification, DNA or histone methylation, gene transcription, protein translation, protein modifications, trafficking of molecules to and from the focal adhesions, epigenetic alterations such as methylation, alterations to cell membranes, transmembrane molecules, cytoskeletal and focal adhesion dynamics, focal adhesions, integrin clustering, adhesion protein activity, localization, and structure, cell-cell adhesion (e.g. cadherins), and pericellular structure and composition.

Formation of Microcavitation Bubble

The below described device, system and method can provide for a non-contact, non-chemical method for the mechanical manipulation of cells and tissues for applications in molecular imaging, high-throughput screening of potentially therapeutic compounds, and/or disease diagnostics. The disclosure can utilize energy, such as for example laser, pulses to generate μCBs as a means to evaluate the activity of physiological mechanical transduction pathways, and thereby screen the cellular response to impulsive mechanical forces. Of course, any energy sources may also be used besides laser pulses, in particular energy sources that can result in μCB formation, e.g., high intensity focused ultrasound created by convergence of acoustic waves from piezoelectric transducers.

In some embodiments, the disclosed screening method can employ a novel, low-cost platform that combines pulsed energy irradiation for the generation of single μCBs to provide precise mechanical stimulation of adherent cells with, for example, dynamic fluorescence imaging for time-resolved measurement of cellular signaling. Embodiments of the disclosed method's use of μCBs to provide cellular exposure to impulsive hydrodynamic flow can avoid the use of pumps, actuators, and microfluidic technologies, any of which would encumber a rapid, high-throughput screening approach. The microcavitation bubble can create a transient and impulsive stress onto cells or a cell culture. The instrumentation as described below for μCB generation can be common, low-cost and easily integrated into existing infrastructure.

In some embodiments, pulsed energy, such as laser microbeams, can offer a fast, non-contact means for cellular manipulation, with the ability to deposit energy with high spatial specificity while minimizing cellular damage. As mentioned above, in some embodiments a standard microscope can focus a short (e.g. nano-, pico-, or femto-second) laser pulse into a 2-D or 3-D cell culture sample. The resulting high intensity radiation and corresponding strong electric fields can cause the generation of free electrons at the focal point. A combination of multiphoton and cascade ionization (e.g. as described in Vogel, A. & Venugopalan, V. Mechanisms of pulsed laser ablation of biological tissues. *Chemical Reviews* 103, 577-644 (2003); Vogel, A., Noack, J., Hüttman, G. & Paltauf, G. Mechanisms of femtosecond laser nanosurgery of cells and tissues. *Applied Physics B* 81, 1015-1047 (2005); Venugopalan, V., Guerra, A., Nahen, K. & Vogel, A. Role of Laser-Induced Plasma Formation in Pulsed Cellular Microsurgery and Micromanipulation. *Physical Review Letters* 88, 1-4 (2002); hereby incorporated in their entirety by reference thereto) can trigger a process known as optical breakdown, which can generate a low to high density of free electrons (e.g. $10^{16}$-$10^{21}$ e⁻/cm³⁾ within the focal volume to form a laser-induced plasma. Plasma formation can lead to vaporization of the aqueous medium within the focal volume, resulting in μCB formation. The plasma energy can also dissipate through a combination of re-radiation, thermal diffusion, and shock wave emission. Thus, while the optical breakdown event is typically confined to the sub-micrometer dimensions of the focal region (depending on the optical parameters), the resulting μCB diameter can range from less than a micrometer to a few millimeters.

In some embodiments, energy can be directed into a cell culture sample to initiate the creation of a μCB. FIG. 1 illustrates an embodiment of a device 100 for initiating the creation of the μCB using a laser, although different types of energy sources can be used. In some embodiments, a laser can be used to create the μCB, however other forms of energy can be used as well. The laser 106 can be, for example, a Nd:YAG laser, though the type of laser is not limiting. The Nd:YAG laser can have λ=532 nm and $E_p$=1-10.5 μJ. The laser can be directed through, for example, a λ/2 wave plate 108, followed by a polarization sensitive beamsplitter 110, and then a linear polarizer 112. This polarized light can then pass through an iris 114 into a dichroic mirror 120, which can be magnified, focused, and directed by a standard microscope 122 into a cell culture sample 104 at a focal point 102. A condenser 124 can also be used. Although these optical components can be used to control the pulse energy and quality of the laser beam, none of them are essential to any particular embodiment. The cell culture can be a monolayer of cells. The laser can be focused using a high numerical aperture objective to a location at about 0, 1, 2, 3, 4, 5, 6, 7, 8, 9, 10, 15, 20, 25, 30, 35, 40, 50, 60, 70, 80, 90, 100, 120, 140, 160, 180, 200 μm above the cell culture. In some embodiments, an ICCD camera 116 can be used with a filter, such as a 570 nm filter 118, to capture the effects of the μCB.

Figure 2:
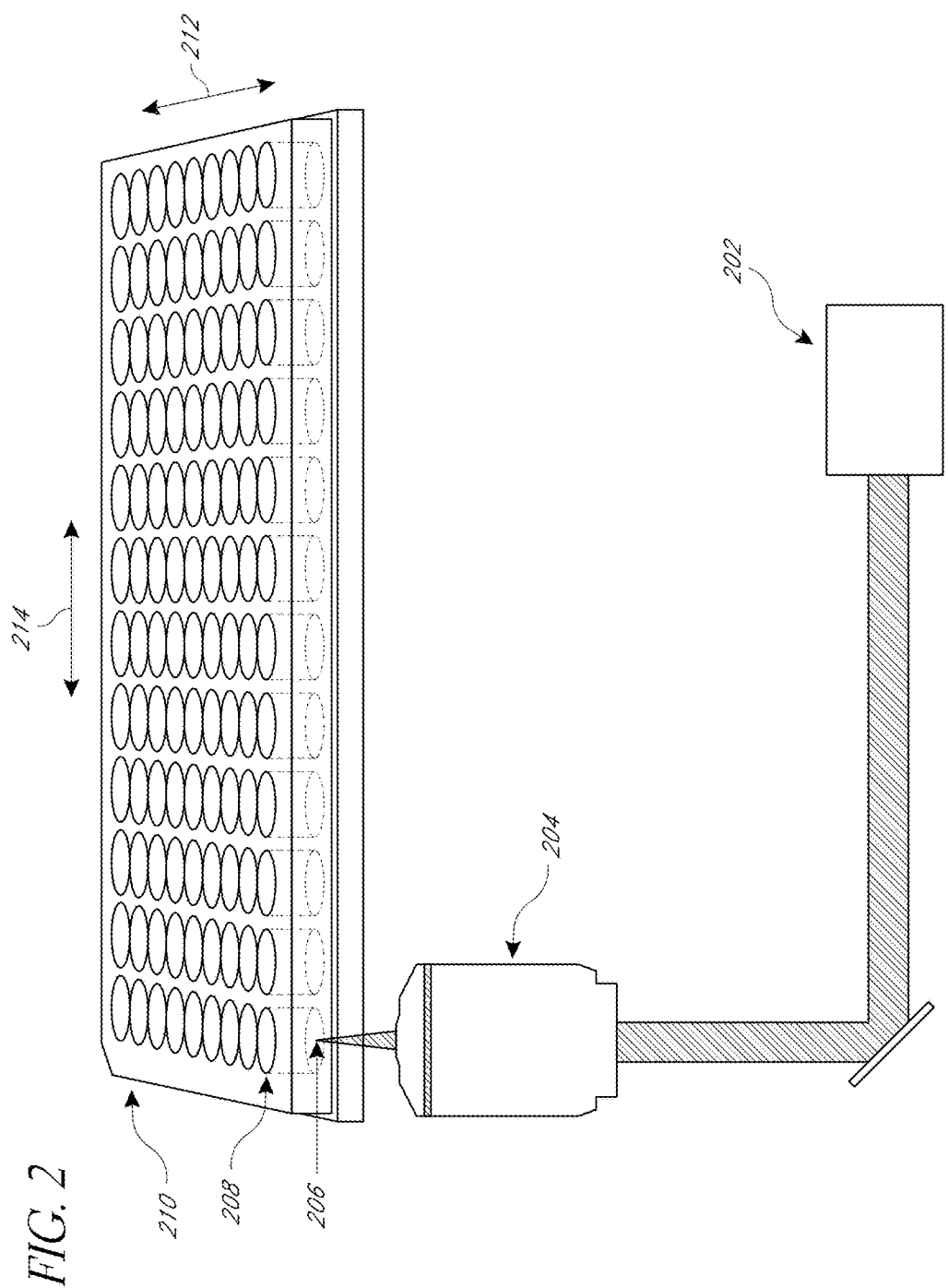
FIG. 2 shows an embodiment of a multi-well setup for high-throughput analysis.

In some embodiments, a plurality of cell culture samples can be provided on a multi-well culture plate. FIG. 2 illustrates an example of such a system. Using, for example, an actuator and controller, the multi-well plate 210 can be moved horizontally along multiple axes 212, 214, in order to precisely position each culture well over the focused energy source 206 from an energy source provider 202 to produce a μCB in the corresponding well 208. As mentioned above, a microscope 204, or other device can be used as well. A sensor can then receive a signal from the sample and produce a numerical or visual output for analysis. The process of positioning each sample well over the energy source can be repeated rapidly and in a highly precise manner, thereby facilitating high-throughput screening of candidate compounds administered to the individual culture wells.

In an alternative embodiment, the multi-well culture plate can remain stationary, and a controller can be used to control the movement of precision optics to focus the energy source toward an individual sample well. The focused energy can initiate a μCB in the corresponding well and the resulting mechanical stimulation of the sample can be analyzed. The controller can then rapidly shift the position of the optics to focus the energy at another sample well, for example the next adjacent well, and the process can be repeated to enable high-throughput analysis of the entire well plate. Alternatively, the system may either include multiple laser sources, or the system optics may split a single laser pulse into multiple beams to simultaneously initiate a μCB in all wells of a multiwall culture dish (e.g., a standard culture dish comprising 1, 2, 6, 12, 24, 48 and 96 wells).

As shown in FIG. 2, a plurality of cell cultures can be used. However, in some embodiments only a single cell culture, or holder for a cell culture, can be used. In some embodiments, the energy source may be applied to a plurality of different cell cultures at the same time. In some embodiments, the platform that the cell cultures are located on can be moved over the energy source. In some embodiments, the energy source itself can be moved. In some embodiments, an intermediate director may be used to apply the energy to the plurality of cells. This intermediate director can be moved alone, or in conjunction with the platform and/or energy source.

In some embodiments, a pulsed laser beam can be incorporated into a commercial image cytometer. Such compatibility with standard image cytometry can allow the disclosed method to be used in standard 2-D cell cultures as well as 3-D tissue matrices. While described above are numerous pieces that can be used with embodiments of a device, not all parts are necessary. In some embodiments, only an energy source and cell culture can be used. Further parts can be added or removed as desired, and a person having ordinary skill in the art would understand the usage and removal of certain pieces.

While described above are devices using a laser energy source, in some embodiments other types of energy sources can be used. For example, other types of energy that can be used include, but are not limited to, mechanical motion, sound, thermal energy, and vibration. In some embodiments, an ultrasonic transducer can be used to form the μCBs. In some embodiments, piezo electric actuation can be used to form the μCBs. However, any energy source can be used that can form microcavitation bubbles.

Dynamics of Microcavitation Bubbles

As shown in FIG. 3A, an embodiment of an optical design can deliver a pulsed laser microbeam above cultured cells, although the location is not limiting. Pulse energy from a source 302 can be adjusted using a half waveplate 304 in front of a linear polarizer 306. A mirror 314 can be used to change the direction of the energy. An iris 310 can be used to select a central, uniform portion of the laser beam. The beam can be reflected by a dichroic filter 314 within an inverted microscope 316 and focused by, for example, a 0.45 NA microscope objective to generate optical breakdown resulting in a µCB 318 within the cell culture 320. Imaging can be performed using a CCD camera 312.

By using a single laser pulse to form a µCB of a desired size, a microtsunami can be generated that provides a customized hydrodynamic shear stress exposure to an adherent cell culture. An embodiment of a device to create the microtsunami, as shown in FIG. 3A, can be easily integrated with commercial microscopes or imaging cytometers by introducing a focused low-energy laser beam into the optical path. Using fluorescence microscopy and reporter molecules, cellular mechano-response resulting from the µCB generated microtsunami can be imaged.

The pressures inside the µCB can cause it to expand rapidly and collapse. In some embodiments, the displacement of aqueous media due to the dynamic expansion and collapse of the µCB can result in a microtsunami. Hydrodynamic analysis of µCB dynamics reveals that cells surrounding the site of energy irradiation can be subject to higher transient mechanical stresses, on a microsecond timescale, relative to physiological values. More specifically, collapse of µCBs can generate hydrodynamic stresses in 2-D fluid media and can generate viscous and elastic stresses in 3-D materials. The 3-D material environments can be, for example, polymers, hydrogels, natural tissues, reconstituted cells, cell cultures and tissues, extracellular matrices, synthetic/natural hybrid materials, and functionalized materials which combine a natural or synthetic matrix such as polyethylene glycol, alginate, polyacrylamide, poly(lactic-co-glycolic acid), and combinations with natural or synthetic molecules with specific biomolecular function. Combinations of the above elements are also applicable.

FIG. 3B illustrates an example of a model that can be used to analyze µCB-generated fluid flow. In FIG. 3B, the luminal surface of a blood vessel 322 is modeled as an endothelial cell monolayer cultured on a glass surface 324. A µCB 326 can be formed on the monolayer 324, which generates a microtsunami and subjects the monolayer sheer stresses that simulate the fluid flow 328 of a blood vessel 322.

Furthermore, hydrodynamic and elasticity modeling of µCB dynamics can show a direct correlation between the location of the cell relative to the center of the µCB and the mechanical stresses to which the cell is exposed. This can allow for a direct correlation between cellular exposure to the laser-generated microtsunami and the subsequent cellular response. The location, amplitude, duration, and spatial extent of the microtsunami can be controlled by changing the optical parameters of the pulsed laser and thus different testing can be performed with different test compounds. Similarly, the shear stress exposures produced by the microtsunami, which are typically microseconds long, can be tuned in duration and amplitude to provide sub- and supra-physiological shear stress impulses in regions greater than about 1, 1.5, 2, 2.5, 3, or 3.5 mm in diameter. In some embodiments, the region affected can be 1, 2, 3, 4, 5, 6, 7, 8, 9, or 10 times the size of the microcavitation bubble. However, the affected region is not limiting.

The Gilmore model can provide a basis upon which to predict µCB dynamics and associated hydrodynamic stresses in fluid environments. The Gilmore model can provide quantitative predictions for the time-resolved bubble wall radius ($R_B(\tau)$) and velocity ($V_B(\tau)$) (refer to FIG. 3C). The model assumes irrotational flow and applies conservation of mass and momentum in a manner that accounts for the effects of fluid inertia, viscosity, compressibility, and surface tension on the µCB dynamics. Time-resolved imaging of laser-generated µCBs has successfully verified the accuracy of Gilmore model predictions. Using this model, the maximum bubble size and fluid medium determine the subsequent µCB dynamics. Because the µCB is responsible for the fluid displacement that mechanically stimulates the adherent cells, the maximum µCB radius ($R_{max}$) can determine the cellular exposure to the hydrodynamic stresses. Thus, the cellular exposure to the hydrodynamic shear stresses can be tuned precisely by adjusting the laser microbeam parameters, such as pulse energy, pulse duration, wavelength, and numerical aperture, to achieve the desired µCB size. For a given numerical aperture increases in µCB size and shear stress magnitude generally are achieved with increases in pulse energy and pulse duration. These are very complex processes with nonlinear interplay between these factors.

Mass conservation, in conjunction with Gilmore model predictions for $R_B(\tau)$ and $V_B(\tau)$, can enable quantification of the cellular exposure to the microtsunami. Specifically, the time resolved velocity ($V_\infty(r,t)$) experienced by an adherent cell located at any radial position from the bubble center, r, larger than $R_{max}$, can be calculated. Once $V_\infty(r,t)$ is determined, momentum conservation is used to calculate the time-resolved shear stress ($\tau(r,t)$), applied to cells at position, r, according to the following equation:

$$\tau(r,t) = \rho\nu\left(\frac{\partial V}{\partial z}\right)\bigg|_{z=0} = \rho\sqrt{\frac{\nu}{\pi}} \int_0^t \frac{\partial V_\infty(r,t')}{\partial t'} \frac{dt'}{\sqrt{t-t'}}$$

Figure 3C:
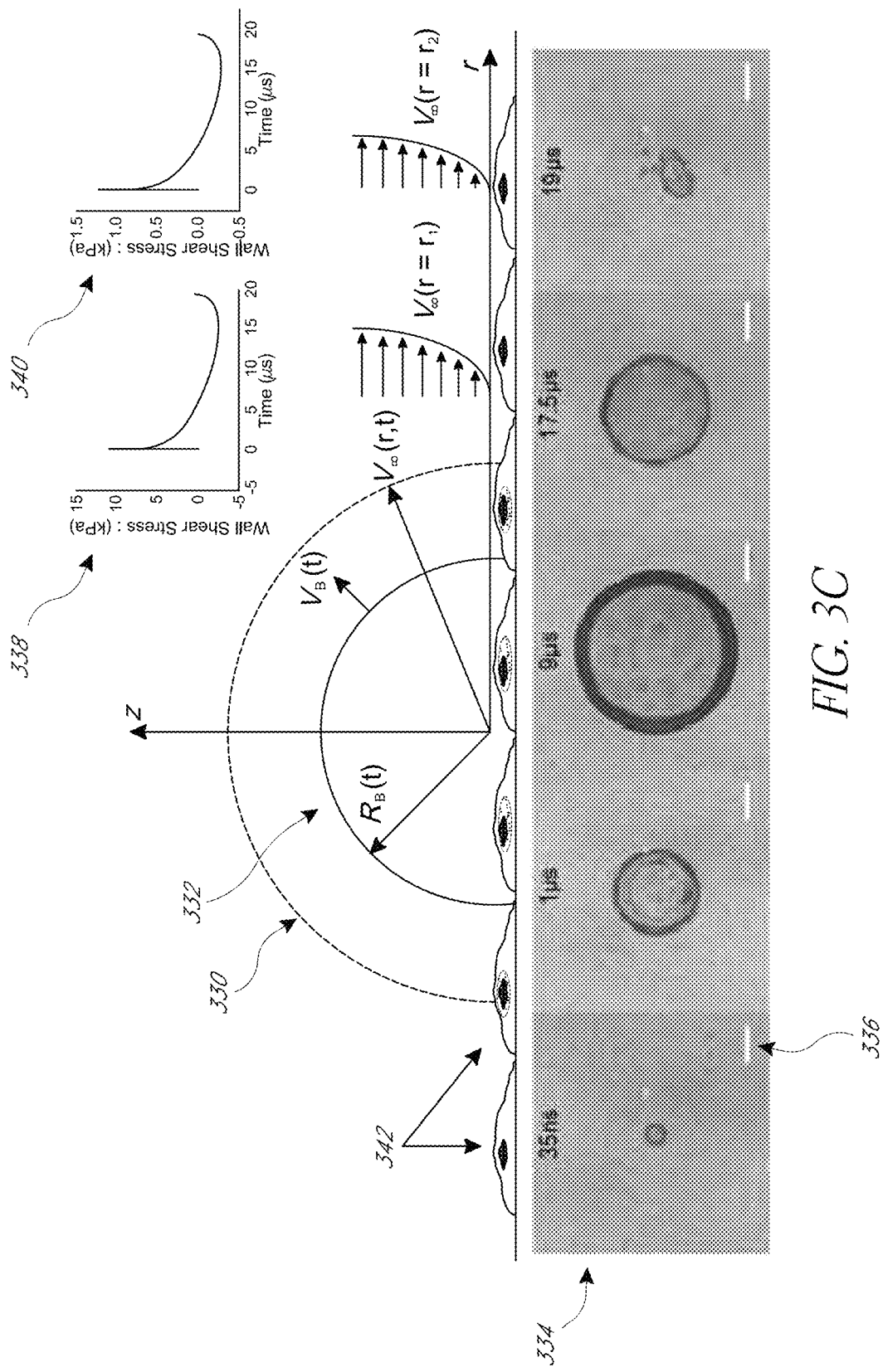
FIG. 3C shows a cross section view through the center of a μCB at time, t, with a μCB wall radius, $R_B(\tau)$, and velocity $V_B(\tau)$.
Figure 3D:
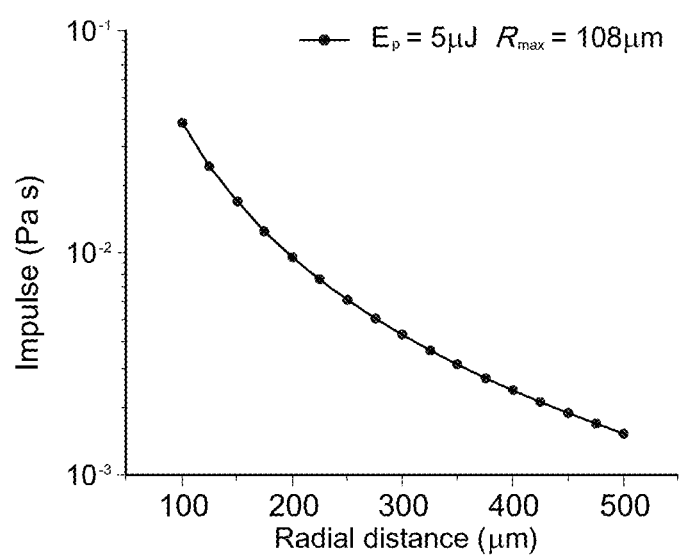
FIG. 3D is a depiction of computed shear stress impulse for μCB with $R_{max}$=108 μm. Physiological range of shear stress impulse spans 0-10 Pa·s.

FIG. 3C shows, for purposes of example only, a plot of $\tau(r,t)$ at radial locations, r equal to 150 µm 338 and 300 µm 340, and generated by a µCB with $R_{max}$ equal to 108 µm. As shown in FIG. 3C, the surrounding fluid moves with velocity $V_\infty(r,t)$ in response to the µCB expansion 330 and collapse 332. The FIG. 3C image panel 334 shows a time-resolved series of a single µCB that reaches $R_{max}$ equal to 108 µm in 9 µs. For reference, the scale bar 336 of the image panel is 50 µm. The µCB shown in FIG. 3C was generated using a single 500 ps duration laser pulse with 5 µJ pulse energy. The resulting fluid flow results in local transient shear stresses that decrease in amplitude with larger radial position, as shown in the graph insets 338, 340. The Gilmore model predicts a reduction in the maximum fluid shear stress with increasing radial distance from the bubble center. While the maximum stresses can be several orders of magnitude larger than physiological shear stresses (e.g. in the circulatory system), they persist for timeframes on the order of millionths of seconds. The local cellular exposure to the mechanical impulse produced by the microtsunami can be determined by integrating the local $\tau(r,t)$ over the entire µCB cycle. This mechanical impulse can be plotted as a function of radial distance, as shown in FIG. 3D. The calculated impulse values are similar in magnitude to those experienced in vitro by HUVECs 342, which range from 0 to 10 Pa·s. As noted above, the impulse magnitude can be easily tuned by varying the µCB diameter. FIG. 3D provides physiological impulse values approaching 0.1 Pa·s using a 5 µJ laser pulse to create a µCB with $R_{max}$ equal to 108 µm. Higher or lower impulse values can be produced using larger or smaller µCB diameters, respectively.

Taken together, embodiments of the disclosed method can provide a robust means for the dosed application of hydrodynamic shear stresses to adherent cell cultures through the precise tuning of laser pulse energy. This method can induce cellular mechanosignaling within a cell culture in response to a microtsunami. For example, mechanosignaling of primary human endothelial cell cultures can be induced, although the type of cell culture is not limiting. In addition, embodiments of the disclosed method can modulate this cellular response using a known chemical inhibitor of mechanotransduction. Taken together, the disclosed method can perform wide-sense screening of test compound libraries to identify those compounds that can alter the activity of mechanotransduction pathways.

Types of Cell Culture Samples

In some embodiments, the cell culture sample can be two-dimensional cell culture, and can consist of, for example, cells adherent to a substrate. In adherent cell cultures, the μCB-initiated microtsunami can produce hydrodynamic shear stresses that can cause cell lysis, necrosis, and molecular delivery in well-defined spatial regions proximal to the μCB. Such microtsunamis can initiate mechanotransduction signaling in adherent cells located in regions extending far beyond both the zone of cellular injury and maximum μCB size. For example, a 108 μm radius μCB can mechanically stimulate cells located within a diameter of approximately 1 mm surrounding the center of the μCB.

In some embodiments, the sample can be three-dimensional, and can consist of, for example, polymers, hydrogels, natural tissues, reconstituted cells, cell cultures and tissues, and/or tissue, extracellular matrices, synthetic/natural hybrid materials, and functionalized materials which combine a natural or synthetic matrix such as polyethylene glycol, alginate, polyacrylamide, poly(lactic-co-glycolic acid), and combinations with natural or synthetic molecules with specific biomolecular function. Combinations of the above elements are also applicable. In these systems, both adjustments to μCB size and extracellular matrix (ECM) composition can expose cells to a broad range of hydrodynamic stresses, including, but not limited to, elastic stresses. The application of laser-generated μCBs and fluorescent probes in 3-D tissue matrices or hydrogels can enable studies of the role of mechanotransduction in processes such as tumor growth and metastasis, traumatic brain injury, stem cell differentiation, and tissue development.

Figure 4A:
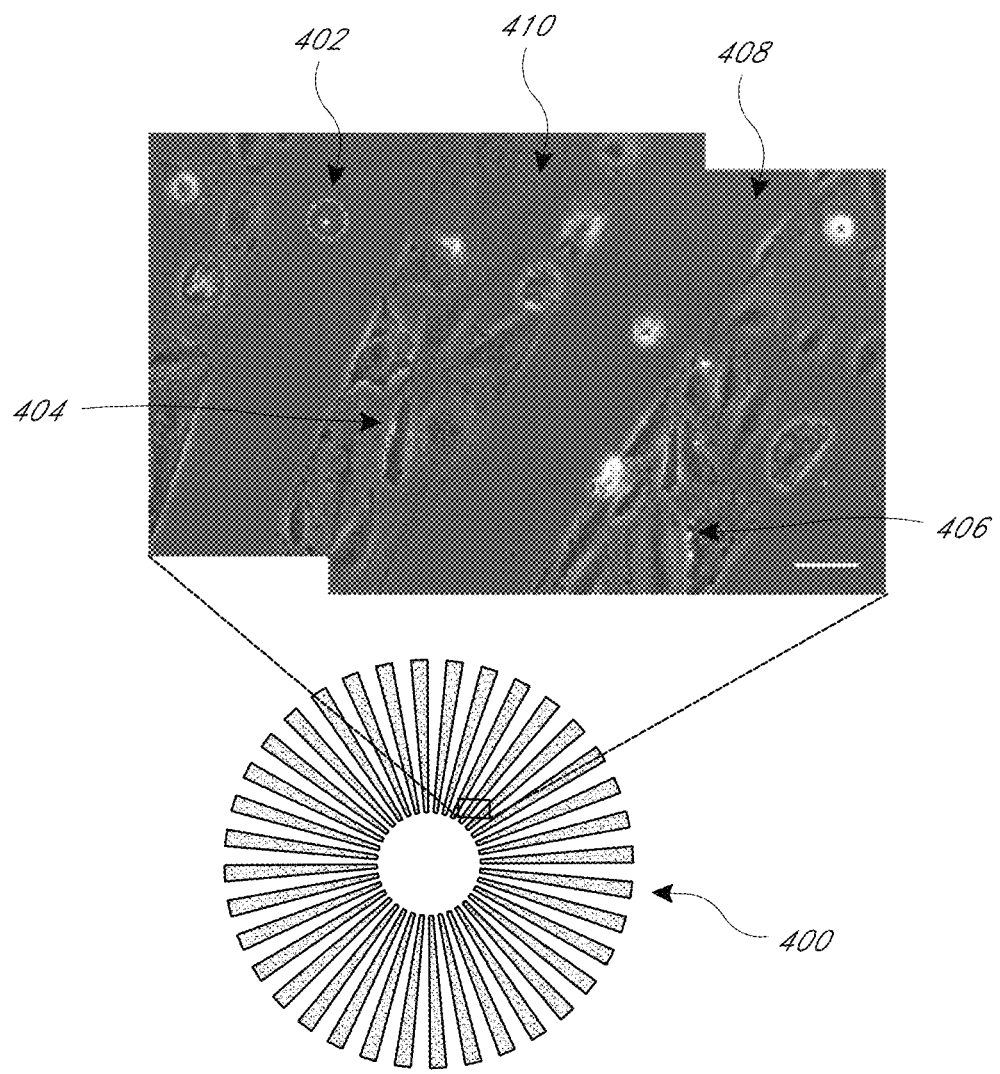
FIG. 4A shows an embodiment of a pinwheel-patterned extracellular matrix (ECM) that includes regions of cells separated by cell-free zones.
Figure 4B:
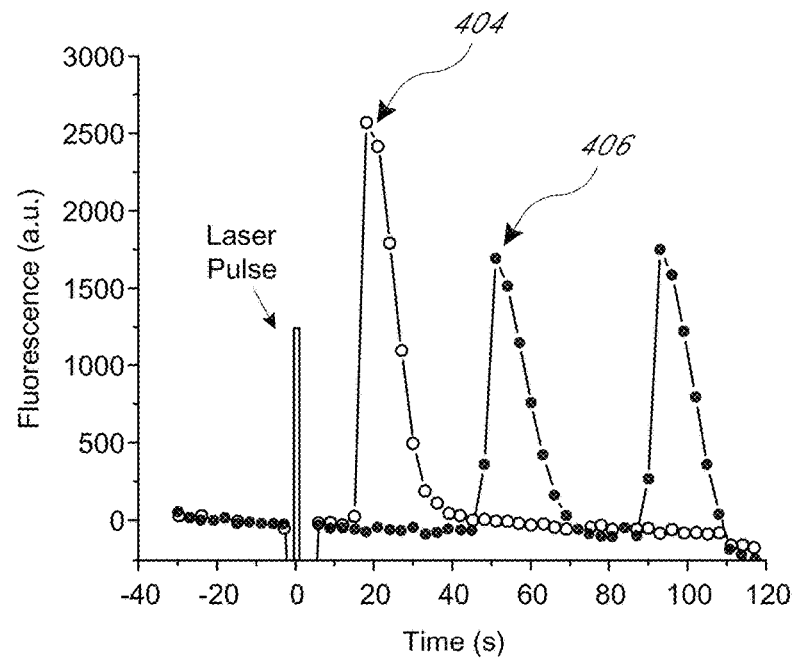
FIG. 4B shows intracellular calcium-mediated fluorescence dynamics for two cells separated by a cell-free zone.
Figure 4C:
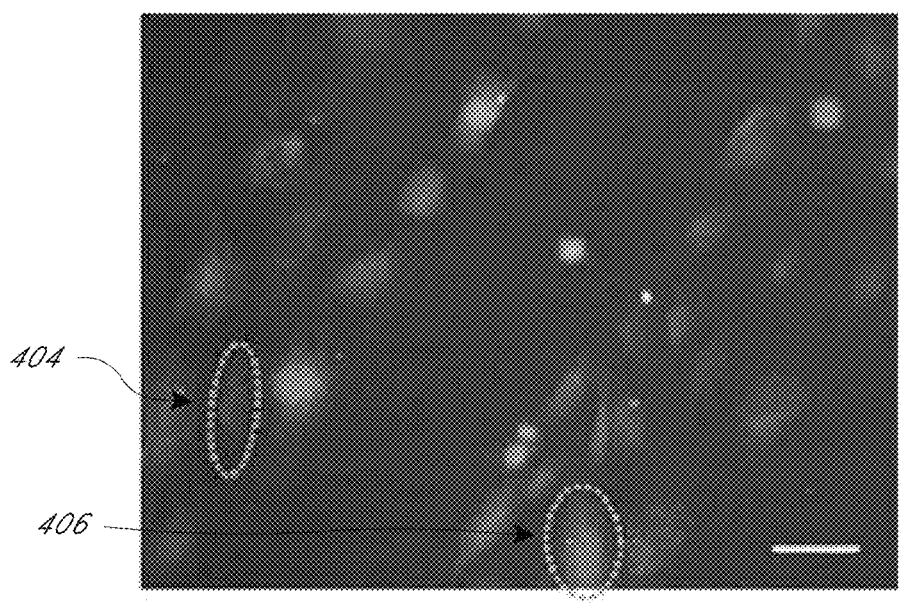
FIG. 4C shows a Fluo-3AM fluorescence image of the cells corresponding to the graphs in FIG. 4B.

In one embodiment, the cell culture sample can comprise cells adherent to a patterned substrate, thereby facilitating analysis of the effect of cell-cell contact on the activity and responsiveness of the mechanotransduction pathway being monitored. Patterning can be achieved using micro-patterned fibronectin or other ECM components. Such micro-patterning can be customized to achieve alternating cell-dense regions and cell-free regions on a single sample. FIG. 4A shows an example of a micro-patterned substrate 400. The pinwheel configuration 400 results in an alternating series of cell-dense 410 and cell-free zones 408. A μCB 402 can be initiated in one of the cell-free zones and the effects of the resulting microtsunami on cells 404, 406 separated by a cell-free zone can be analyzed. The results, FIG. 4A-C are described in further detail below.

Method of Analysis and/or Screening

As described in detail above, the disclosed method can use pulsed laser microbeam irradiation to induce optical breakdown in a cell culture, which can lead to μCB formation. Subsequent collapse of the μCB can generate a microtsunami, which is a transient microscale impulse of hydrodynamic shear stress. The microtsunami can propagate through the cell culture sample, thereby mechanically stimulating cells extending far beyond the radius of the μCB. Cellular exposure to this stimulus can be tailored through cell-patterning techniques, and standard imaging cytometry methods and fluorescent probes can be employed to monitor the cellular response to the stimulus.

Further, as described above, a μCB above a cell culture can generate a microtsunami, which propagates through the cell culture and causes impulsive mechanical stimulation of the surrounding cells. In this way, the disclosed method creates fluid flow across a sample without relying on bulk flow dynamics or the use of microfluidic devices. The ability to cause mechanical stimulation in this manner enables novel approaches to high-throughput screening, whereby test compounds suspected of modulating cellular mechanotransduction are analyzed in a rapid, highly precise manner. By applying hydrodynamic and elastic stresses in the fashion described above, and using imaging cytometry techniques, an immediate readout of the responsiveness of an entire cell population due to external mechanical impulses can be analyzed. Further, the disclosed method can avoid any thermal effects on cell cultures because the thermal energy associated with the μCB dissipates in the region immediately adjacent to the bubble, and does not transfer into the cells or other material contained in the sample.

Figure 5:
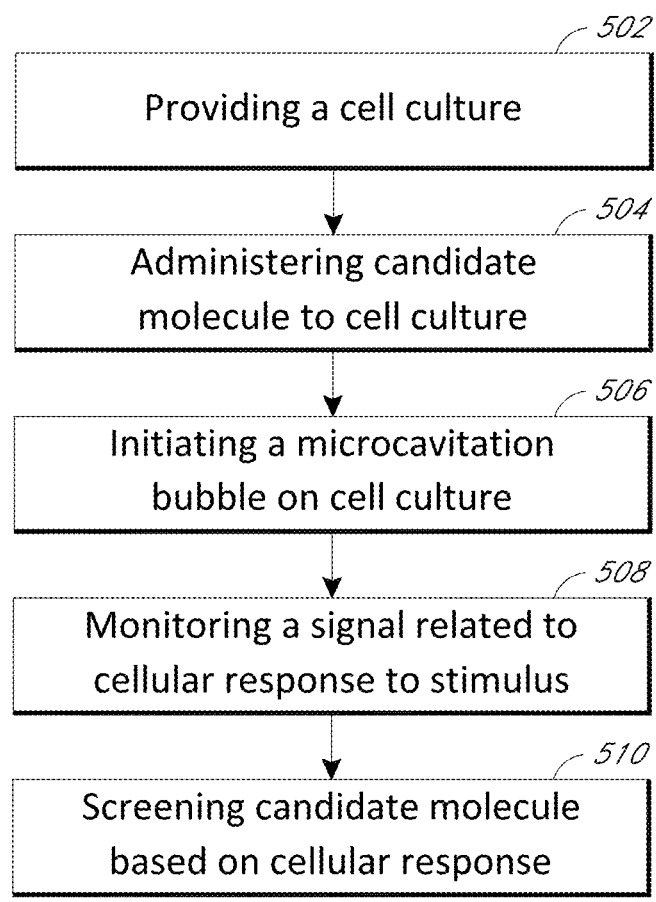
FIG. 5 is a flow diagram of an embodiment of the disclosed method.

As shown in FIG. 5, embodiments of such screening methods comprise: providing a cell culture 502; administering a test compound to said cell culture 504; generating a μCB on said cell culture 506; monitoring a signal related to a cellular transduction pathway 508; and screening the test compound model based on the observed signal 510.

In some embodiments, the effects of the μCB bubble can be analyzed for any effects external to the bubble. This can include effects directly outside the diameter of the bubble, as well as distances away from the bubble. Because the energy of the microtsunami can dissipate at a distance away from the original bubble, an impulsive mechanical stress gradient can be delivered to the cell culture, and therefore a gradient of effects can be analyzed. The stress gradient could mean that different cells could feel different mechanical stresses throughout the cell culture, and the relative effects between and among regions of the sample could be analyzed. This can be unlike, for example, a constantly applied stress to the cell culture which may not allow for analysis of the gradient effect.

In some embodiments, the effects of the microcavitation bubble can be analyzed for inside the bubble. This can include whether the cells survive the microtsunami of the microcavitation bubble, or other effects.

In some embodiments, different mechanotransduction effects can be analyzed after the formation of a microtsunami in a sample. For example, the direct effects of the microtsunami, such as milliseconds from formation, can be analyzed. However, the screening is not limiting to this, and numerous so called downstream effects can be analyzed. For example, the effects of the microtsunami may be felt during later cellular mitosis, which can occur seconds, minutes, hours, days, or even months from the initial microtsunami. The disclosed method can therefore be used to screen and discover the effects of the microtsunami on a cell culture at any time point, whether it is immediately after the microtsunami or much later.

Different types of cellular affects can be analyzed and/or screened using the disclosed method. The type of cellular response studied is not limiting. For example, signaling, kinase activity, tyrosine kinase dynamics (e.g. FRET sensors and antibodies), molecular trafficking, cytoskeletal arrangement, cytoplasmic translocation, membrane potential changes, translocation of transcription factors across the nuclear envelope, molecular dynamics (e.g. trafficking, release of molecules from a cellular compartment, active transport, membrane fluidity, for example, the YAP-TAZ pathway in which transcriptional factors are transported into the nucleus downstream of mechanostransduction), mRNA expression (gene expression, genetic networks), chromatin modification, DNA or histone methylation, gene transcription, protein translation, protein modifications, trafficking of molecules to and from the focal adhesions, epigenetic alterations such as methylation, alterations to cell membranes, transmembrane molecules, cytoskeletal and focal adhesion dynamics, focal adhesions, integrin clustering, adhesion protein activity, localization, and structure, cell-cell adhesion (e.g. cadherins), and pericellular structure and composition.

In some embodiments, numerous microtsunamis can be formed in the same cell culture. This way, certain effects, such as hysteresis caused by the repeated mechanical stresses, can be analyzed. In some embodiments, only one microtsunami is formed in the cell culture. In some embodiments, the microtsunamis are formed in all of the cell cultures at the same time, though in some embodiments there may be time differences in the formation of microtsunamis in the cell cultures.

In some embodiments, the disclosed method can be used on more than one cellular samples. These cellular samples can be, for example, in the same container, or in numerous separate containers, for example, in separate wells of a multi-well culture dish. Some of the cell cultures may be used as "control" groups, not containing any test compound in them (only the vehicle), while other cell cultures can may be used as "treatment" groups, having test compound in the vehicle; both the control and treatment groups are subjected to the same induced mechanical stress. In some embodiments, another set of cellular samples (both control and treatment groups) can be used; these are not subjected to any induced mechanical stress. Therefore, it can be seen whether the responses measured relate to mechanotransduction, and whether the mechanotransduction is modulated by the test compound. Likewise, it can be seen whether other factors, such as changes in cell media, temperature, or other external factors, contribute to the measured response. Therefore, it can be quickly determined what the effect of the test compound could be on the cell cultures after microtsunamis are formed in all of the cultures. In some embodiments, microtsunamis may not be formed in all of a plurality of cell cultures.

In some embodiments, the use of standard fluorescence imaging of calcium ($Ca^{2+}$) signaling can provide a simple readout of real-time cellular mechanotransduction. Some embodiments can employ multi-channel imaging to enable the simultaneous measurement of other fluorescent molecules that probe mechanotransduction processes, such as nitrous oxide (NO) production, kinase activity (e.g. by genetically encoded FRET sensors), and membrane potential.

In some embodiments, microtsunami-initiated mechanosignaling can be consistent with G-protein-coupled receptor stimulation resulting in $Ca^{2+}$ release by the endoplasmic reticulum. Moreover, dose-dependent modulation can occur for $Ca^{2+}$ signaling through exogenous administration of a known inhibitor (2-APB) to this pathway. The imaging of upstream signaling and its modulation by exogenous molecules demonstrates embodiments of the disclosed method's ability to initiate and assess cellular mechanosignaling in real-time. Embodiments of the high-throughput screen disclosed below illustrate the effects of test compounds on cellular mechanotransduction using standard imaging cytometry.

EXAMPLES

Laser Microscope

μCBs were created using the $\lambda=532$ nm emission of a Q-switched pulsed microchip laser (PNG-M03012, Teem Photonics) emitting pulses 500 ps in duration. The laser beam is expanded and collimated and the pulse energy of the collimated beam is controlled using the combination of a $\lambda/2$ waveplate and polarizing beam splitter. The central portion of the beam is selected by an iris and directed into an inverted microscope (Olympus IX-81) by a dichroic (Chroma ZT532NBDC) mirror. The beam is then focused by a 20×, 0.45 numerical aperture microscope objective (Olympus IX-81). The laser microbeam was focused approximately 10 μm above the cell monolayer.

Fluorescence microscopy was performed on the same inverted microscope using epifluorescence illumination from a mercury short-arc lamp (X-Cite 120PC, Lumen Dynamics). The filter cube containing a 480/40 excitation, 535/50 emission, and 505 LP dichroic filters (Chroma) which were chosen based on the fluorescent probe specifications. The fluorescence emission was focused onto a CCD camera (Hamamatsu ORCA R2) mounted onto the left side port. Image acquisition was controlled using μmanager software.

Time resolved imaging of the bubble cycle was achieved using a gated ICCD camera (Stanford Computer Optics, 4 Picos). Time resolved image illumination was provided by delivery of a short pulse of light at the desired time delay following the arrival of the pulsed laser microbeam to the aqueous sample. The image illumination was provided by the fluorescence emission of a dye cell that was pumped by a Q-switched frequency doubled Nd:YAG laser (Quantel Brilliant B). The emission of the dye cell was captured by an optical fiber and directed to the condenser of the microscope. Timing between the laser, camera gate, and dye cell emission was controlled using a delay pulse generator (BNC 575, Berkeley Nucleonics Corp.), and the corresponding electronic signals were monitored by an oscilloscope (TDS 2024, Textronix).

Cell Preparation

Primary adherent human umbilical vein endothelial cells, HUVECs were grown in EGM-2 (endothelial cell growth media), supplemented with EGM-2 BulletKit (Lonza). The cells were cultured in 35 mm #1.5 cover glass bottom culture dishes (WPI) coated with fibronectin (Sigma).

Intracellular Calcium Probe Loading and Monitoring

The cells were loaded with Fluo-3/AM (Molecular Probes) as per manufacturers specifications. The cells were incubated in Hank's Balanced Salt Solution HBSS with ions and 6 μM Fluo-3/AM for 60 min at room temperature, after which the cells were allowed to incubate for 30 min in EGM-2. The cells were rinsed with HEPES buffered Hank's Balanced Salt Solution without calcium supplemented with $Mg^{2+}$ (HHBSS) and 3 mM EGTA (Sigma) to chelate traces of extracellular calcium. Imaging of intracellular calcium resulting from exposure to μCB was performed at room temperature using HHBSS with EGTA as the medium.

Cellular Substrate Patterning

Patterning of the cellular substrate with fibronectin was accomplished using standard soft lithography and microfluidic techniques suitable for ECM patterning in specific regions. Cellular adhesion in regions lacking fibronectin was prevented using Pluronic F-127 (Sigma).

Agonist and Inhibitor

For verification of cell viability and signaling reliability, endoplasmic reticulum (ER)– stored calcium was released by the addition of ATP (50 µM, Sigma) after each experiment. For the IP3 inhibition experiments, the ER calcium release was suppressed in a dose dependent manner by the addition of 10-100 µM 2-Aminoethoxydiphenyl borate, (2-APB, Sigma).

HCS Preparation 96 well plates (Invitro-Scientific) were coated with fibronectin and P4 HUVECs were plated in each well. 2-APB was added using the same concentrations as above, PP2 (Sigma) was added at a concentration of 10M and Verapamil (Sigma) was added at a concentration of 50 nM. DMSO was also added as a control corresponding to the highest amount added from solution of the drugs, 0.3%. The first seven columns contained the previously used HHBSS– with 3 mM EGTA and the last five columns contained HHBSS+ supplemented with 2 g/L D-glucose.

Cell Lysate Preparation

HUVECs grown in a tissue culture flask at full confluency were resuspended in standard HBSS– at a concentration of $1.5 \times 10^7$ cells/mL. Cell lysate solution was prepared by subjecting this solution to repeated freeze-thaw cycles at −80° C. and then sonicated on ice for 30 s.

Example of Cellular Response Using Src Kinase

The disclosed method of using laser-generated cavitation bubbles to induce a response in a cell sample was shown to have the ability to successfully activate a cellular biochemical pathway in response to mechanical stress. For example, Src kinase has been shown to be influence the transduction of mechanical stimuli through cell adhesions and focal complexes in the cell. A Foerster resonance energy transfer (FRET)-based biosensor capable of detecting Src kinase activation was used as described in greater detail below.

Description of FRET and the Src Kinase Biosensor

FRET occurs between two fluorophores if they are in sufficient proximity and if the emission spectrum of the donor fluorophore sufficiently overlaps the excitation spectrum of the acceptor. Any change of the distance and/or relative orientation between the two fluorophores may affect the efficiency of FRET and therefore the ratio of acceptor to donor emission. Studies have shown that fusion proteins with interacting peptide partners sandwiched between two different fluorescent proteins (FPs) are capable of monitoring various cellular events in live cells with high spatial and temporal resolution.

Figure 6:
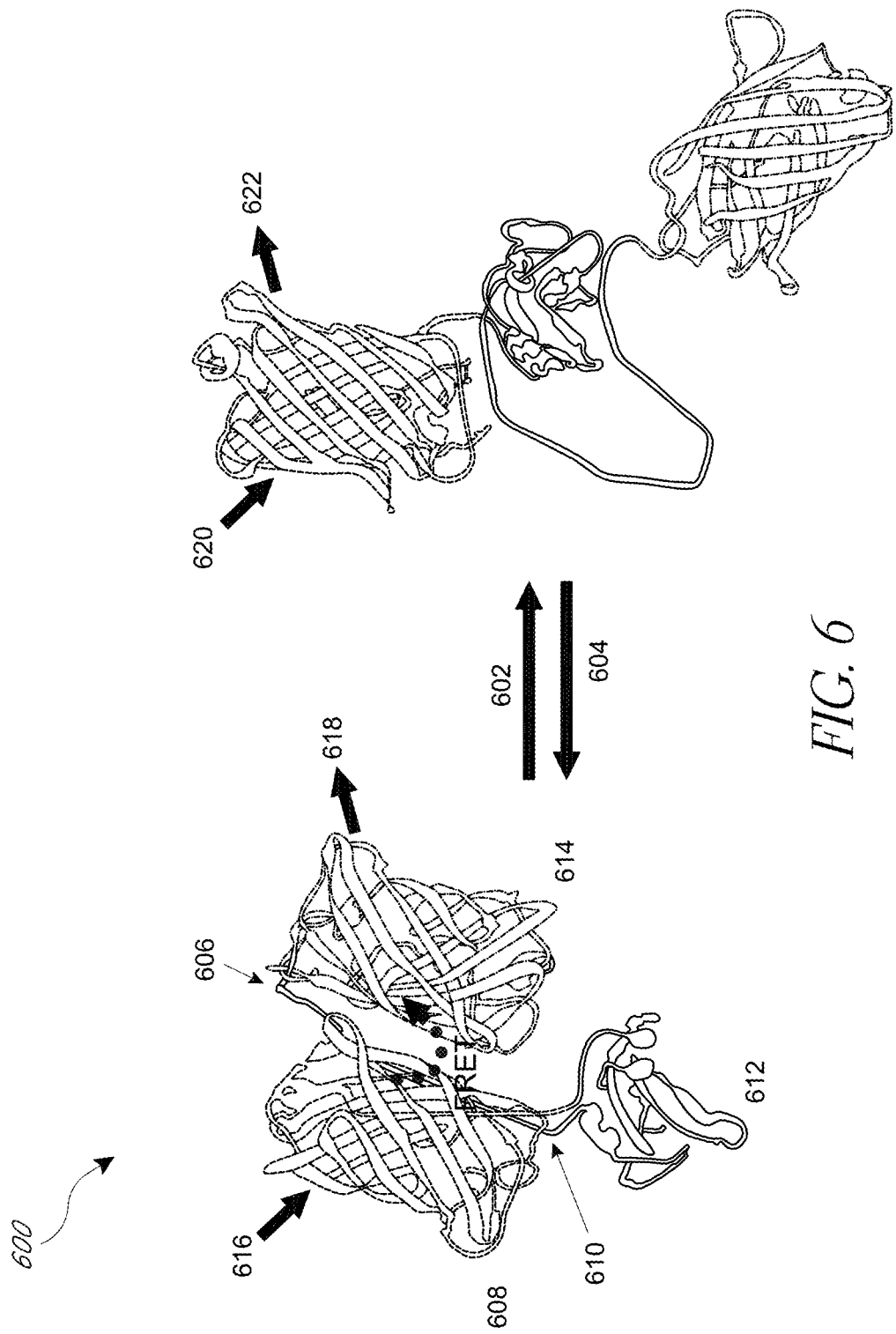
FIG. 6 illustrates a schematic representation of an Src reporter showing the FRET effect of the Src reporter upon the actions of Src kinase or phosphatase.

A FRET-based biosensor capable of detecting Src kinase activation 600 was used in this example. This genetically-encoded biosensor is a Src substrate peptide with cyan and yellow fluorescent proteins (CFP and YFP, respectively) attached in close proximity to yield a high FRET. As depicted in FIG. 6, upon Src phosphorylation, the CFP and YFP are separated, thus decreasing the FRET. There can be a substrate 606 and a linker 610 to, for example Sh2 612. There can also be EYFP 614. The molecules can have respective sizes 433 nm 616 and 527 nm 618. Src phosphorylation 602 has the effect of separating the CFP 608 and YFP 614 to form a new structure having sizes of about 433 nm 620, and 476 nm 622, whereas the activity of phosphatase 604 has the opposite effect, increasing the FRET.

Experimental Procedure

Bovine aortic endothelial cells (BAEC) were cultured using standard cell culture techniques and grown to 80% confluence in polystyrene culture dishes with glass bottoms in Advanced DMEM with Glutamax (Invitrogen) and transfected with the Src reporter using Fugene 6 (Roche). Cells were imaged in bright-field and trans-fluorescence both before and after (within 2 minutes) the laser pulse delivery to the cell sample. Image processing was conducted in Matlab and the CFP/YFP intensity ratio was computed to determine the FRET signal.

Results

Figure 7A:
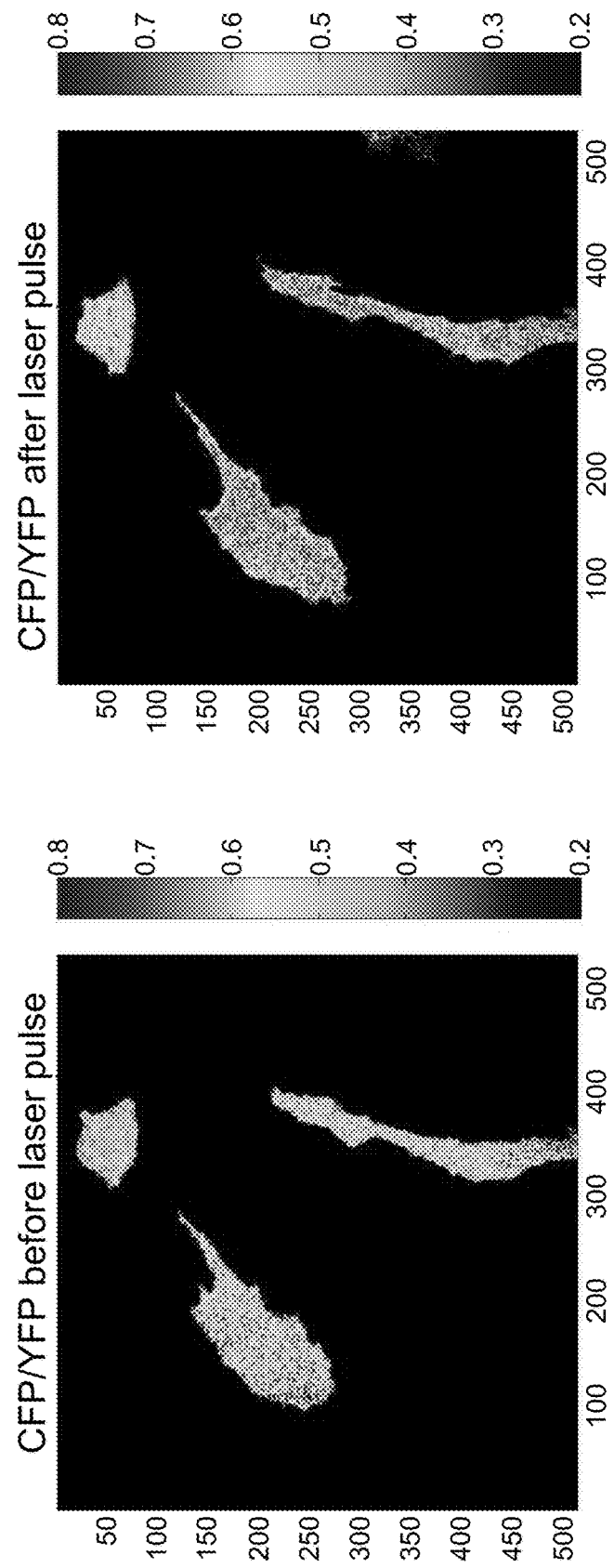
FIG. 7A depicts images showing the ratio of CFP/YFP emission of cells positioned 740 microns away from the site of laser irradiation before and after a 10.5 μJ, 1100 ps pulse.
Figure 7B:
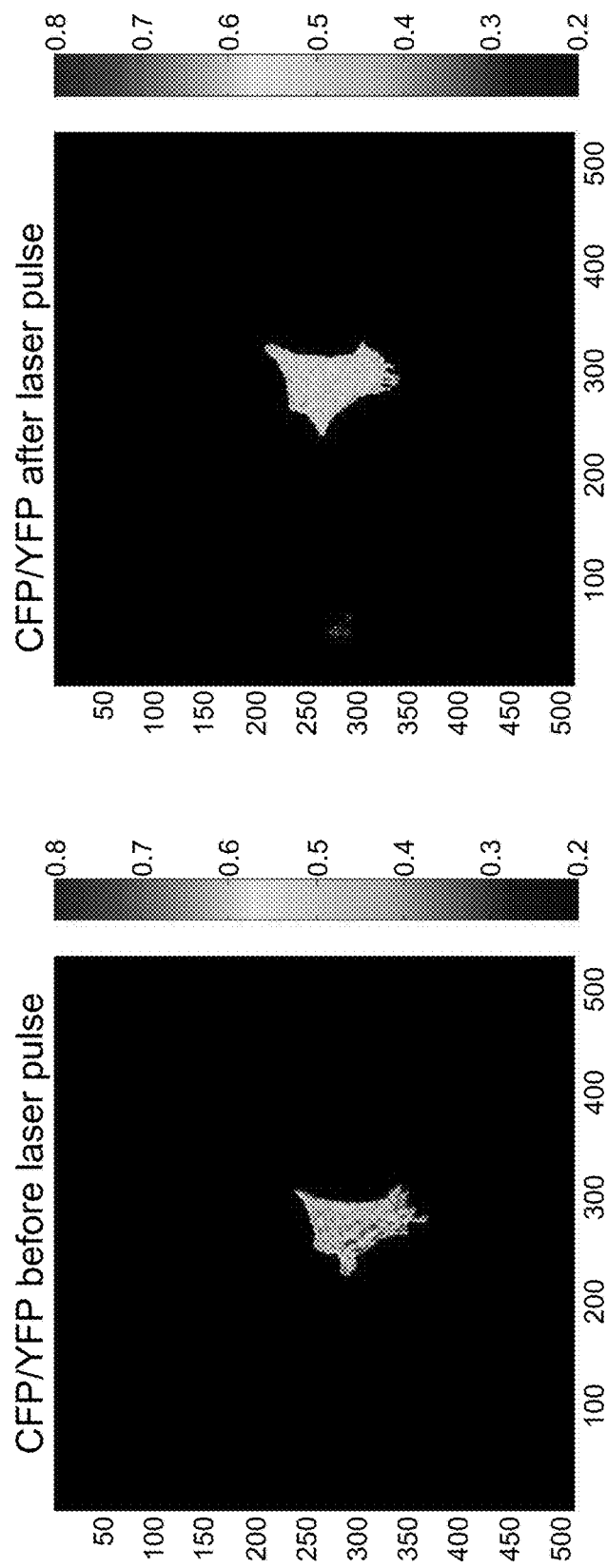
FIG. 7B depicts images showing the ratio of CFP/YFP emission of cells positioned 200 microns away from the site of laser irradiation before and after a 10.5 μJ, 1100 ps pulse.

After testing, a decrease in FRET was found, indicated by an increase in the CFP/YFP ratio, in cells following the laser pulse at distances up to 1 mm away from the site of laser irradiation when using a pulse duration of 1100 ps and a pulse energy of 10.5 µJ. The test results are shown in FIGS. 7A & 7B. As shown in the figures, a definite increase in intensity of the ratio of CFP to YFP emission can be seen after the laser pulse was fired, indicating activation of the Src kinase and a biochemical response to the cavitation bubble-induced shear stress.

Description of Fluo3-AM, ($Ca^{2+}$ Sensitive Fluorescent Dye to Report Mechanosignaling)

In another example, Fluo3-AM probes, rather than FRET probes that report Src kinase activation, were used. Fluo3-AM is a $Ca^{2+}$ sensitive fluorescent dye capable of reporting mechanosignaling in primary HUVECs. The probability of cell signaling to the cellular exposure of hydrodynamic impulse was related using the Gilmore bubble model and cell patterning techniques were used to control and examine the impact of cell-cell contacts on the resultant mechanosignaling dynamics.

To examine the cellular response to laser-generated microtsunamis, a classical model system of vascular mechanotransduction was employed in which the release of $Ca^{2+}$ ions from the endoplasmic reticulum (ER) of primary HUVECs was monitored fluorescently. Intracellular calcium regulates processes downstream of mechanotransduction in HUVECs, including the production of nitric oxide (NO) and the activation of Src Kinase, both of which are hallmarks of mechanotransduction.

The endothelial cells (ECs) are in direct contact with blood flow, where they experience a complex mechanical microenvironment subject to normal and shear (τ) stresses resulting from pulsatile blood flow. Vascular mechanotransduction regulates EC alignment to flow, vascular homeostasis, flow resistance, and vascular morphogenesis and pathogenesis. Moreover, changes in shear stress have been demonstrated to result in EC NO production and downstream vasodilation. The complex shear stress fields produced by turbulent flow can be correlated with the progression of atherosclerosis, which involves the upregulation of proinflammatory genes and downregulation of lipid metabolism as linked to vascular mechanotransduction. Endothelial cells have several classes of mechanosensory molecules such as stretch-activated ion-channels, receptor tyrosine kinases, junction proteins and integrins. The activation of these stretch-sensitive molecules can initiate signaling cascades and can lead to the synthesis and release of autocrine and paracrine factors, cell proliferation, migration, differentiation and apoptosis. Given that mechanotransduction plays a prominent role in the cardiovascular system, for both physiological homeostasis and the induction of disease, primary HUVEC culture represents an appropriate system in which to explore the ability of test compounds to alter the activity of specific mechanotransduction axes. Below describes an embodiment of a method to stimulate a mechanotransduction pathway using µCB-generated microtsunamis and to alter that pathway's sensitivity to hydrodynamic stresses using a known chemical inhibitor.

HUVECs were cultured to confluence on glass bottom Petri dishes and were labeled with Fluo-3 AM, a fluorescent reporter whose emission increases upon binding to cytoplasmic $Ca^{2+}$. Prior to exposure to the μCB-generated microtsunami, the cell culture media was replaced with $Ca^{2+}$-free HEPES-buffered Hank's balanced saline solution (HHBSS) supplemented with 3 mM EGTA, to ensure chelation of extracellular $Ca^{2+}$ ions. In this way, any observed signaling could be attributed to $Ca^{2+}$ release from the ER and not from $Ca^{2+}$ transport across plasma membrane ion channels. A single 500 ps, 5 μJ pulsed laser microbeam was delivered to the cell culture forming a μCB with $R_{max}$=108 μm. The μCB resulted in cellular exposure to a microtsunami with spatially varying mechanical impulse as shown in FIG. 3D.

Figures 8C, 8D:
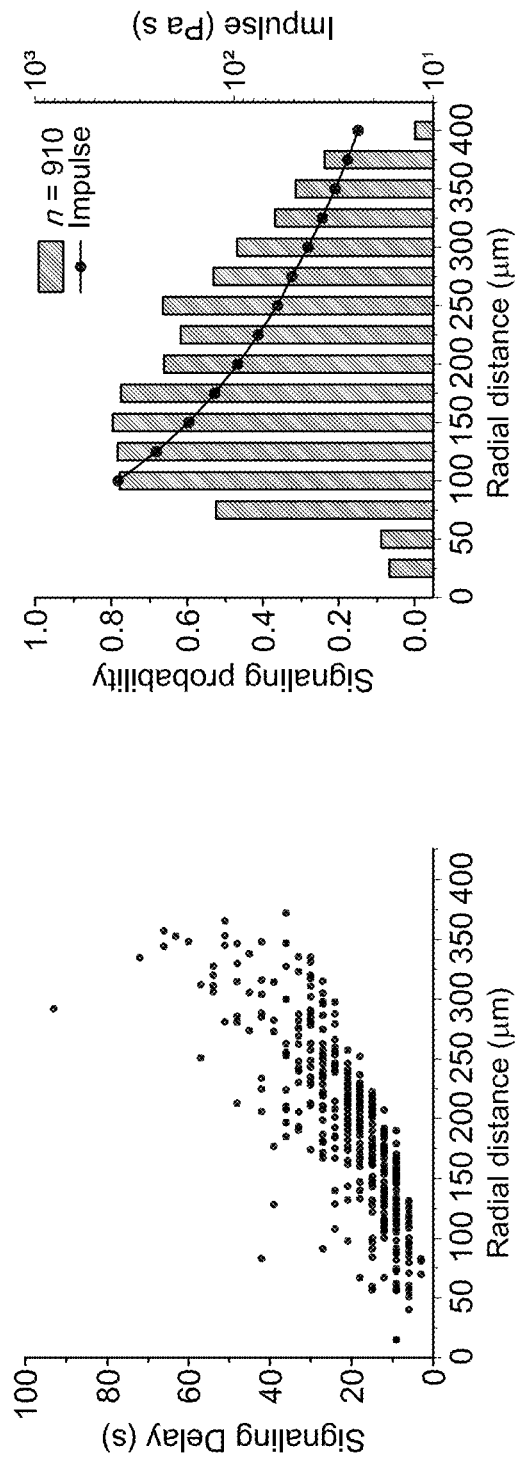
FIG. 8C depicts calcium signaling delay versus radial distance from the μCB center for the 447 cells which signal out of a total of 765 cells monitored in 5 separate experiments.
FIG. 8D shows a histogram presenting the signaling probability and shear stress impulse as a function of radial distance from the μCB center. The probability of signaling is maximum at radial distances of r=100-175 μm and decreases with the mechanical impulse.

FIG. 8A shows a Fluo-3AM time series of cytoplasmic calcium release in HUVECs in response to a single μCB generated microtsunami over a confluent monolayer. The μCB with $R_{max}$=108 μm was generated at the position indicated by the green circle. The μCB had a maximum radius of 108 μm. The 0 sec time point is immediately prior to the delivery of the laser pulse to the cell culture. Subsequent images use this time point for background subtraction. Scale bar, 50 μm. As shown in FIG. 8A, the microtsunami produced by a single μCB 800 initiated $Ca^{2+}$ signaling in many surrounding cells, where the onset of $Ca^{2+}$ release from the ER can be dependent upon cell position relative to the pulsed laser microbeam. For example, cells located at distances approximately 60, 150, 240 μm from the pulsed laser microbeam showed an increasing delay in the initiation of signaling, as shown in FIG. 8B. In fact, a systematic increase in signaling delay time with distance from the pulsed microbeam was found (see FIG. 8C), where the speed of this $Ca^{2+}$ wave can be estimated from the slope of a linear regression as 4.5±0.3 μm/s (95% confidence interval). Even cells immediately adjacent to the pulsed laser microbeam can have a signaling delay of several seconds following the expansion and collapse of the μCB, which occurs within 20 μs. Therefore, the available concentration of a diffusible intracellular mediator within each cell can be modulated by the magnitude of the locally applied shear stress impulse. The intracellular transport of such a mediator could result in the observed signaling delay, and decreasing signaling probability with increasing distance from the center of the μCB, as shown in FIG. 8D. The low signaling probability observed for cells nearest to the μCB could likely be due to cell lysis or transient membrane permeabilization. At larger distances, a monotonic relationship can be observed between the decreasing shear stress impulse and the probability of $Ca^{2+}$ signaling. At the close, cells were dosed with 50 μM ATP to confirm that the cells remain responsive to chemical stimulation of ER $Ca^{2+}$ release.

Figure 9A:
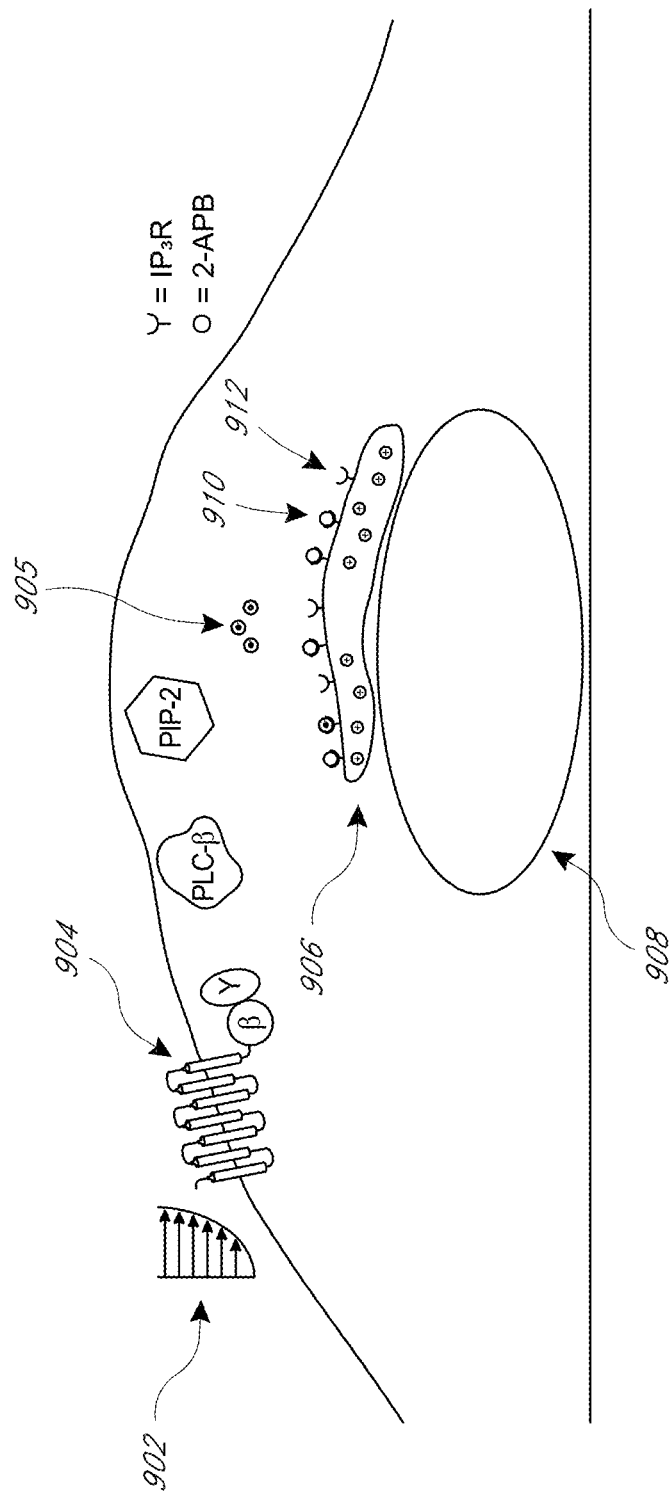
FIG. 9A Depiction of putative signaling pathway for microtsunami-induced calcium release where apical fluid shear stress leads to the production of IP3, which diffuses to the ER, binds to the IP3 receptor (IP3R) and stimulates calcium release. 2-APB competitively binds to the IP3R.

Embodiments of the above described method show sensitivity to changes in mechanosignaling with the addition of a putative inhibitor of the observed mechanotransduction pathway. FIG. 9A depicts one such pathway. For example, microtsunami exposure 902 was tested as either directly or indirectly stimulating G-protein coupled receptors 904 at the apical surface, which in turn could lead to the production of IP3 905 that diffuses to the ER where it binds the IP3 receptor 912 on surface 906 by nucleus 908 and stimulates $Ca^{2+}$ release (FIG. 9A).

The observed mechanosignaling was consistent with G-protein coupled receptor stimulation at the apical cell surface. This leads to the production of IP3, which diffuses to the ER where it binds the IP3 receptor and initiates $Ca^{2+}$ release. Microtsunami-stimulated $Ca^{2+}$ signaling was shown to be suppressed using a known inhibitor, 2-APB, 910, to this pathway, and through the use of a patterned substrate (see FIG. 4A) to which the cultured cells adhere, that mechanosignaling may not require cell-cell contact throughout the cell culture.

Figure 9B:
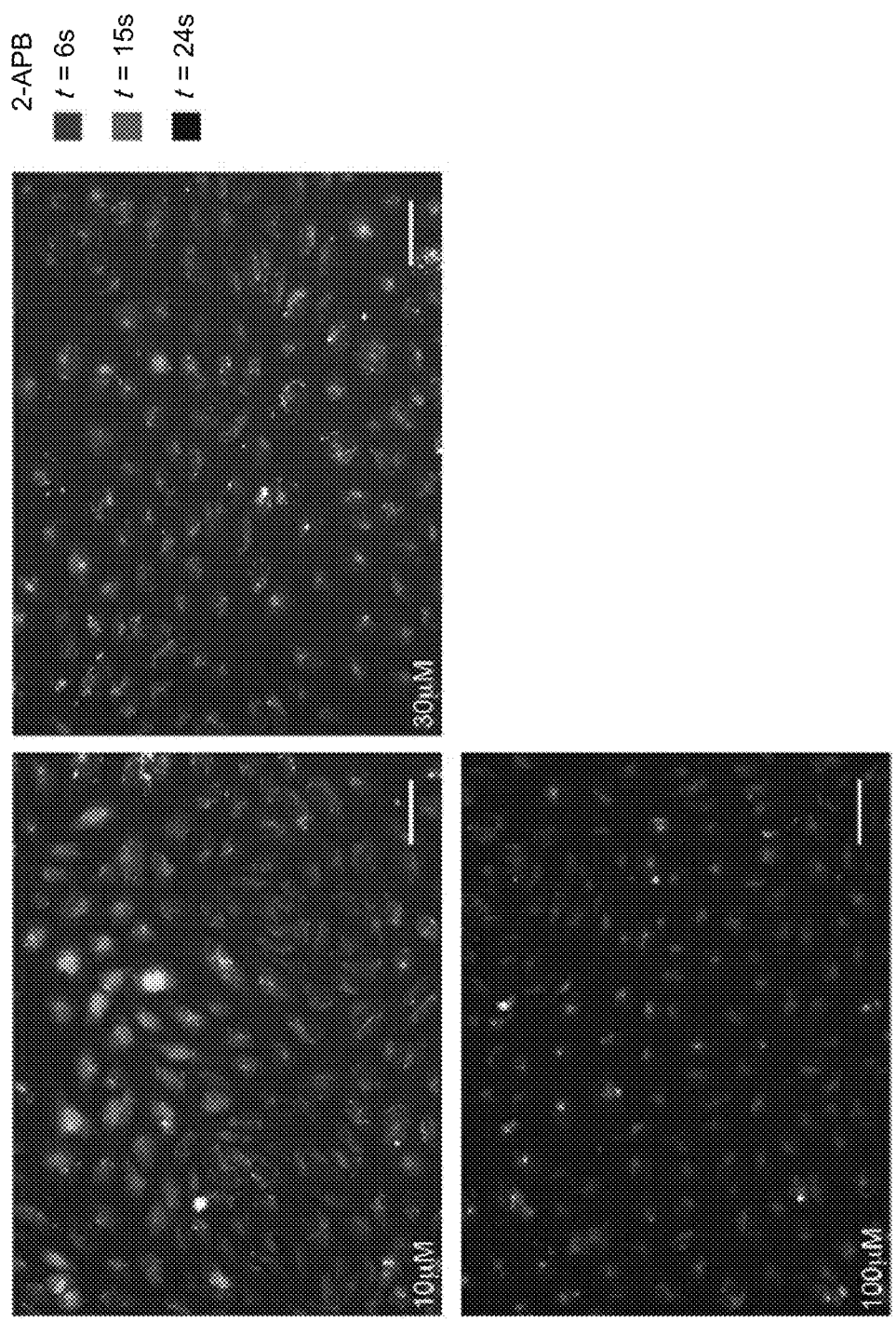
FIG. 9B shows fluorescence images (Fluo-3AM) of μCB generated calcium signaling following incubation in 10, 30 or 100 μM 2-APB.
Figure 9C:
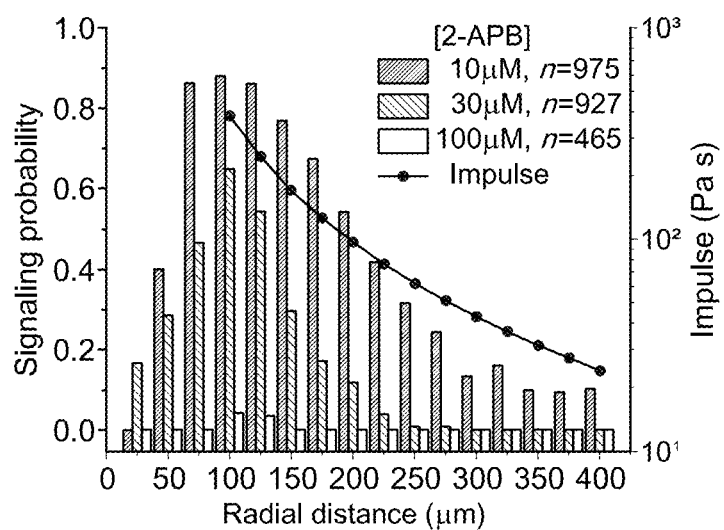
FIG. 9C depicts microtsunami-induced calcium signaling in HUVECs that is sensitive to 2-APB.

The experiment was repeated in the presence of 2-APB (2-Aminoethoxy-diphenyl borate), a known inhibitor of IP3, which acts by competitively binding the IP3 receptor (see FIG. 9A, 910). FIG. 9A depicts the putative signaling pathway for microtsunami-induced calcium release where apical fluid shear stress leads to the production of IP3, which diffuses to the ER, binds to the IP3 receptor (IP3R) and stimulates calcium release. 2-APB competitively binds to the IP3R. HUVECs were cultured to confluence and incubated with 2-APB at concentrations of 10 μM, 30 μM or 100 μM, previously shown to provide dose-dependent inhibition of $Ca^{2+}$ release following stimulation using a bolus of ATP. It was found that 2-APB attenuates the spatial and temporal extent of $Ca^{2+}$ signaling in a dose-dependent manner, as shown in FIG. 9B. FIG. 9C summarizes results from many trials and quantifies the attenuation of both the signaling probability and spatial extent with increasing 2-APB concentration and decreasing shear stress impulse. The data demonstrates the ability of the disclosed method to mechanically stimulate cells and measure downstream signaling in real time while being sensitive to the action of exogenous molecules such as 2-APB, which can interfere with a clinically important mechanotransduction axis.

Figure 9D:
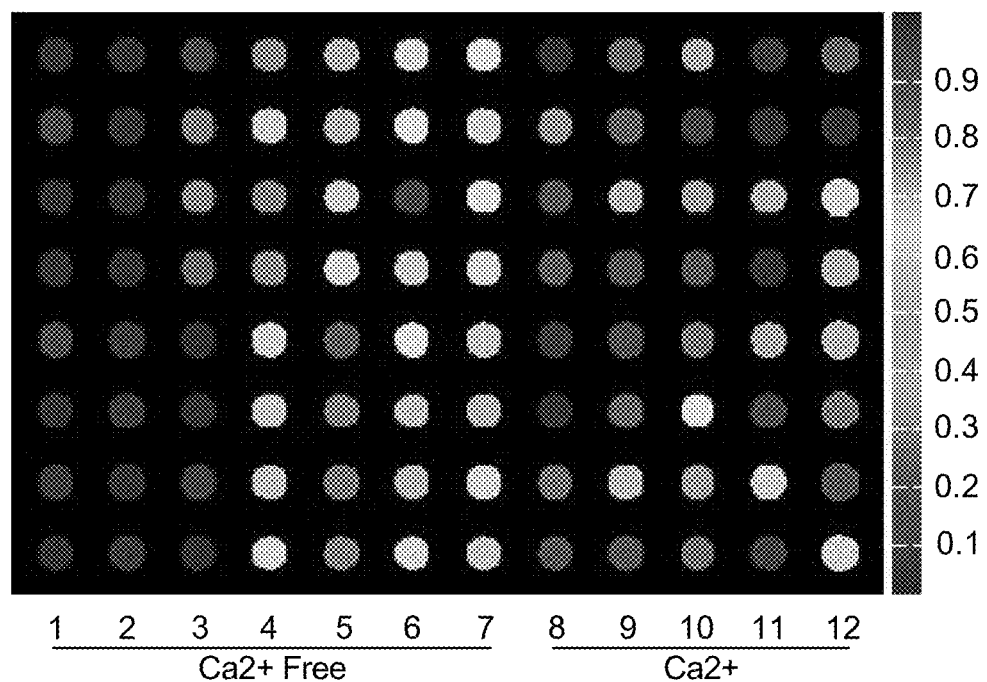
FIG. 9D depicts the experimental results for an array of cell culture wells and shows the percentage of cells in each well that exhibit calcium signaling 100-150 μm away from the center of a μCB.

The experiments were performed in a 96-well plate where twelve conditions, each with eight replicates, were tested for their potential effect on μTsunami generated $Ca^{2+}$ signaling. Conditions included within this screen was the addition of three test compounds: (i) PP2 (phosphoprotein phosphatase 2), a known Src family kinase inhibitor, (ii) Verapamil, a voltage-dependent calcium channel blocker used to treat hypertension, and (iii) 2-APB, a known inhibitor of $IP_3$ induced $Ca^{2+}$ release used above. FIG. 9D shows the percentage of cells in each well exhibiting calcium signaling in the annular region positioned 100-150 μm away from the center of the μCB. The total time necessary to screen all 96 wells was constrained by the latency in the $Ca^{2+}$ signaling dynamics that requires us to image each well for 35 seconds following microtsunami exposure (FIG. 9D). This results in a total screening time of 56 min, a speed that is unprecedented for the completion of 96 independent mechanotransduction measurements, each of which assayed, on average 34 cells in the annular region examined. The results of this screen confirm the dose-dependent inhibitory effect of 2-APB on microtsunami-induced mechanosignaling (FIG. 9D, columns 1-3) while neither PP2 nor Verapamil (FIG. 9D, columns 4, 5) affected $Ca^{2+}$ signaling in $Ca^{2+}$ free media. This result was expected, as only 2-APB is specific to the ER $Ca^{2+}$ release. Moreover, positive control lanes, which included the addition of DMSO or $Ca^{2+}$ free media alone (FIG. 9D, columns 6,7), demonstrate normal activation of cellular mechanotransduction. FIG. 2c, columns 8-12, tested cells in $Ca^{2+}$ containing media and demonstrated suppression of signaling with addition of 2-APB (FIG. 9D, column 8). However, significant microtsunami-induced mechanosignaling was observed in the presence of Verapamil or PP2 (FIG. 9D, columns 9,10) as well as in the control lanes that included the addition of DMSO or $Ca^{2+}$ containing media alone (FIG. 9D, columns 11,12).

To demonstrate that the observed cellular response was due to mechanotransduction from embodiments of the disclosed method, the possibility that either: (i) cells are stimulated by cell lysate created near the center of the bubble and transported to distal cells, or (ii) cells immediately proximal to the bubble are mechanically stimulated, while cells further away are indirectly stimulated through diffusion-mediated processes that rely on cell-cell contact was addressed. This may be relevant since the speed of the calcium wave was similar to that reported for a sheet of endothelial cells where only a single cell was mechanically stimulated by a micropipette tip.

Exposure to cell lysate alone was confirmed as not responsible for the observed $Ca^{2+}$ dynamics. Cells were dosed with a solution of cell lysate immediately following microtsunami exposure. In addition, cells were exposed to cell lysate alone. As positive controls, the $Ca^{2+}$ signaling response produced by ATP was measured with and without microtsunami exposure. As a negative control, $Ca^{2+}$ signaling without cell lysate, ATP, or microtsunami exposure was measured. While ATP elicited the expected strong $Ca^{2+}$ signaling response, the administration of cell lysate consistently resulted in minimal $Ca^{2+}$ signaling comparable to the negative controls and independent of μTsunami exposure.

Figure 10:
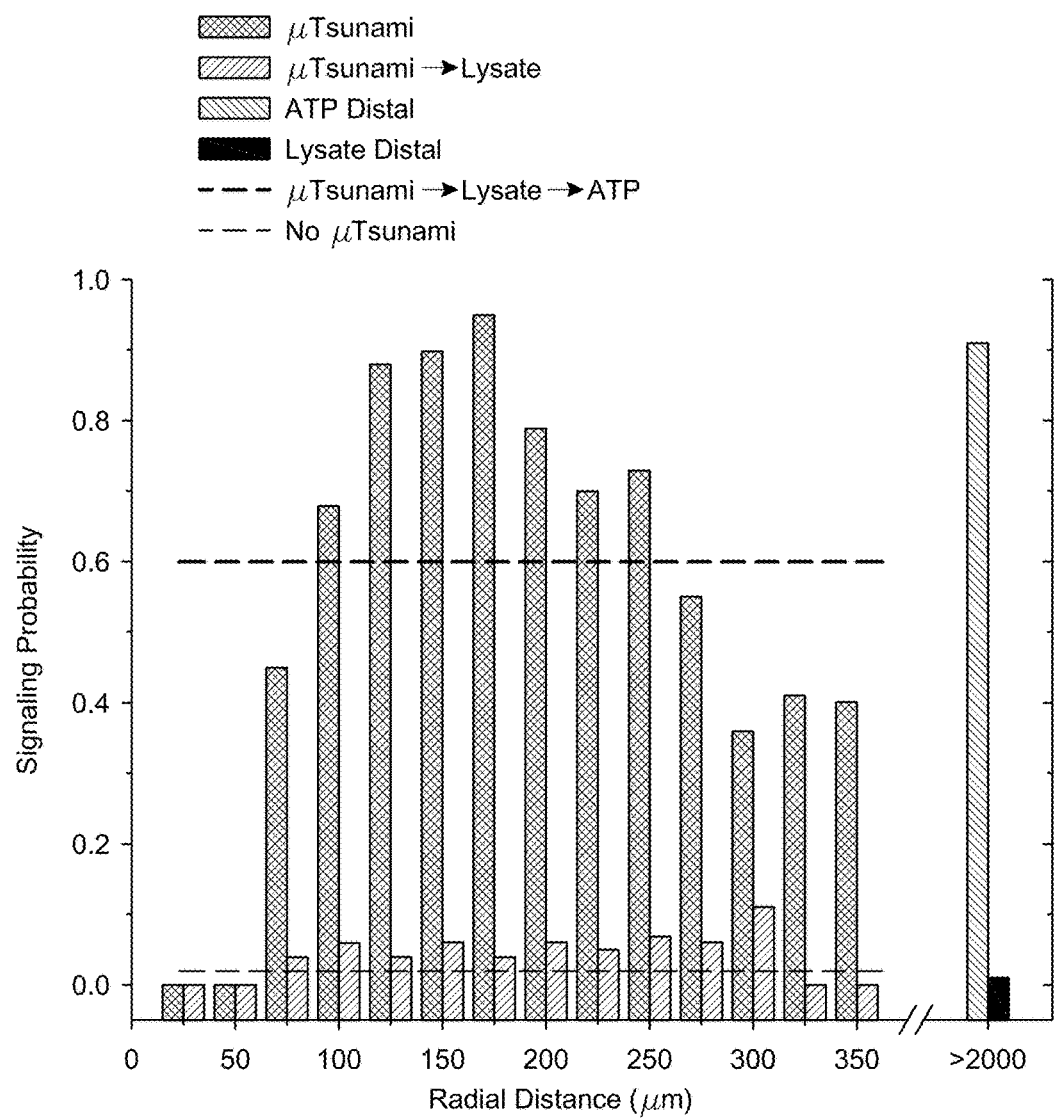
FIG. 10 shows a graph of $Ca^{2+}$ signaling as a function of distance from the site of microbeam irradiation.

FIG. 10 shows a graph which demonstrates that cellular exposure to cell lysate alone does not stimulate observed $Ca^{2+}$ signaling. Probability of Ca2+ signaling produced by microtsunami exposure is plotted as a function of distance from the site of laser microbeam irradiation. Two control experiments were conducted to test whether the observed $Ca^{2+}$ was due to cellular exposure to cell lysate produced by the microtsunami. In the first, 150 μL of cell lysate was administered following a $Ca^{2+}$ signaling event generated by microtsunami exposure. The degree of signaling observed in this experiment was comparable to the negative control of no laser irradiation as well as the second negative control experiment that administered cell lysate without microtsunami exposure. Both experiments elicited an average signaling probability of <1%. By contrast, cellular exposure to the microtsunami alone resulted in an average signaling probability of 52% for all cells located within 350 μm of the site of laser irradiation. A positive control experiment of ATP-stimulated $Ca^{2+}$ signaling immediately following the microtsunami resulted in an average signaling probability of 60%, whereas ATP stimulation in the absence of the microtsunami resulted in an average signaling probability of >90%. The reduced ATP signaling probability following microtsunami exposure was due to cell lysis/necrosis produced by the microtsunami.

Cell-cell contact was confirmed as not responsible for the observed $Ca^{2+}$ dynamics. As shown in FIG. 4A, HUVECs were cultured on glass-bottom Petri dishes that were patterned with fibronectin 400. The laser microbeam was delivered within a cell-free region sufficiently large to exclude cells from the zone of lysis thus eliminating the production of cell lysate. $Ca^{2+}$ signaling was observed in an adjacent cell-populated region 404, as well as in a second region 406 that was separated from the first by another cell-free zone 408. FIGS. 4B & 4C show Ca2+ signaling over time corresponding to each cell-populated region, 404, 406. This result demonstrates that the $Ca^{2+}$ signals can propagate across regions free of cell-cell junctions leaving mechanotransduction as the primary mechanism of stimulation in the second region. Therefore the observed cellular mechanotransduction does not rely on cell-cell contact throughout the entire cell culture. Furthermore, during the μCB expansion, cell lysate is dispersed to the periphery of the expanding bubble but concentrated again by the laminar flow associated with the μCB collapse. For confluent cultures, it is unlikely cells outside the μCB are exposed to lysate[41] during the duration of imaging. These patterned substrate experiments demonstrate similar mechanotransduction activity in the absence of cell lysate.

Although the foregoing disclosure has shown, described, and pointed out the fundamental novel features of the present teachings, it will be understood that various omissions, substitutions, and changes in the form of the detail of the apparatus as illustrated, as well as the uses thereof, may be made by those skilled in the art, without departing from the scope of the present teachings. Consequently, the scope of the present teachings should not be limited to the foregoing discussion, but should be defined by the appended claims.

REFERENCES

Each of the following references and US patents is incorporated herein in its entirety by reference thereto.
1. Wang, Y., Botvinick, E., Zhao, Y, Berns M., Usami, S., Tsien, R., & Chien, S. Visualizing the mechanical activation of Src. *Nature* 434, 10401045 (2005).
2. Peyton, S. R., Raub, C. B., Keschrumrus, V. P. & Putnam, A. J. The use of poly(ethylene glycol) hydrogels to investigate the impact of ECM chemistry and mechanics on smooth muscle cells. *Biomaterials* 27, 4881-93 (2006).
3. Kumar, S., Maxwell, I., Heisterkamp, A., Polte, T., Lele, T., Salanga, M., Mazur, E., & Ingber, D. Viscoelastic retraction of single living stress fibers and its impact on cell shape, cytoskeletal organization, and extracellular matrix mechanics. *Biophysical Journal* 90, 3762-73 (2006).
4. Discher, D. E., Janmey, P. & Wang, Y. Tissue cells feel and respond to the stiffness of their substrate. *Science* 310, 1139-43 (2005).
5. Ingber, D. E. Tensegrity: the architectural basis of cellular mechanotransduction. *Annual Review of Physiology* 59, 575-99 (1997).
6. Jaalouk, D. E. & Lammerding, J. Mechanotransduction gone awry. *Nature Reviews Molecular Cell Biology* 10, 63-73 (2009).
7. Orr, A. W., Helmke, B. P., Blackman, B. R. & Schwartz, M. A. Mechanisms of mechanotransduction. *Developmental Cell* 10, 11-20 (2006).
8. Ingber, D. Mechanobiology and diseases of mechanotransduction. *Annals of Medicine* 35, 564-577 (2003).
9. Hahn, C. & Schwartz, M. A. Mechanotransduction in vascular physiology and atherogenesis. *Nature Reviews Molecular Cell Biology* 10, 53-62 (2009).
10. Gottlieb, P. A., Suchyna, T. M., Ostrow, L. W. & Sachs, F. Mechanosensitive ion channels as drug targets. *Current Drug Targets CNS and Neurological Disorders* 3, 287-95 (2004).
11. Huh, D., Hamilton, G. A. & Ingber, D. E. From 3D cell culture to organs-on-chips. *Trends in Cell Biology* 21, 745-54 (2011).
12. Apic, G., Ignjatovic, T., Boyer, S. & Russell, R. B. Illuminating drug discovery with biological pathways. *FEBS Letters* 579, 1872-7 (2005).
13. Drews, J. Drug Discovery: A Historical Perspective. *Science* 287, 1960-1964 (2000).
14. Rudin, M. & Weissleder, R. Molecular imaging in drug discovery and development. *Nature Reviews Drug Discovery* 2, 123-31 (2003).
15. Charras, G. T. & Horton, M. A. Single cell mechanotransduction and its modulation analyzed by atomic force microscope indentation. *Biophysical Journal* 82, 2970-81 (2002).

16. Chien, S. Effects of disturbed flow on endothelial cells. *Annals of Biomedical Engineering* 36, 554-62 (2008).
17. Valberg, P. A. & Butler, J. P. Magnetic particle motions within living cells. Physical theory and techniques. *Biophysical Journal* 52, 537-50 (1987).
18. Chen, C. S., Mrksich, M., Huang, S., Whitesides, G. M. & Ingber, D. E. Geometric control of cell life and death. *Science* 276, 1425-8 (1997).
19. Rau, K. R., Quinto-Su, P. A., Hellman, A. N. & Venugopalan, V. Pulsed laser microbeaminduced cell lysis: time-resolved imaging and analysis of hydrodynamic effects. *Biophysical Journal* 91, 317-29 (2006).
20. Hellman, A. N., Rau, K. R., Yoon, H. H. & Venugopalan, V. Biophysical response to pulsed laser microbeam-induced cell lysis and molecular delivery. *Journal of Biophotonics* 1, 24-35 (2008).
21. Vogel, A. & Venugopalan, V. Mechanisms of pulsed laser ablation of biological tissues. *Chemical Reviews* 103, 577-644 (2003).
22. Vogel, A., Noack, J., Hüttman, G. & Paltauf, G. Mechanisms of femtosecond laser nanosurgery of cells and tissues. *Applied Physics B* 81, 1015-1047 (2005).
23. Venugopalan, V., Guerra, A., Nahen, K. & Vogel, A. Role of Laser-Induced Plasma Formation in Pulsed Cellular Microsurgery and Micromanipulation. *Physical Review Letters* 88, 1-4 (2002).
24. Vogel, A. Nonlinear absorption: intraocular microsurgery and laser lithotripsy. *Physics in Medicine and Biology* 42, 895-912 (1997).
25. Stevenson, D. J., Gunn-Moore, F. J., Campbell, P. & Dholakia, K. Single cell optical transfection. *Journal of the Royal Society, Interface* 7, 863-71 (2010).
26. Gilmore, F. R. The Growth or Collapse of a Spherical Bubble in a Viscous Liquid. *Office of Naval Research* (1952).
27. Knapp, R. T., Daily, J. W. & Hammitt, F. G. *Cavitation*. (McGraw-Hill: New York, 1970).
28. Vogel, A., Busch, S. & Parlitz, U. Shock wave emission and cavitation bubble generation by picosecond and nanosecond optical breakdown in water. *The Journal of the Acoustical Society of America* 100, 148 (1996).
29. Vogel, A., Linz, N., Freidank, S. & Paltauf, G. Femtosecond-Laser-Induced Nanocavitation in Water: Implications for Optical Breakdown Threshold and Cell Surgery. *Physical Review Letters* 100, 1-4 (2008).
30. Lokhandwalla, M. & Sturtevant, B. Mechanical haemolysis in shock wave lithotripsy (SWL): I. Analysis of cell deformation due to SWL flow-fields. *Physics in Medicine and Biology* 46, 413-37 (2001).
31. Malek, A. M., Alper, S. L. & Izumo, S. Hemodynamic shear stress and its role in atherosclerosis. *JAMA: The Journal of the American Medical Association* 282, 2035-42 (1999).
32. Davies, P. F. Flow-mediated endothelial mechanotransduction. *Physiological Reviews* 75, 519-60 (1995).
33. Tran, Q. K. & Watanabe, H. Calcium signalling in the endothelium. *Handbook of Experimental Pharmacology* 2, 145-87 (2006).
34. Kuchan, M. J. & Frangos, J. A. Role of calcium and calmodulin in flow-induced nitric oxide production in endothelial cells. *The American Journal of Physiology* 266, C628-36 (1994).
35. Okuda, M., Takahashi, M., Suero, J., Murry, C., Traub, O., Kawakatsu, H., & Berk, B. Shear stress stimulation of p130(cas) tyrosine phosphorylation requires calciumdependent c-Src activation. *The Journal of Biological Chemistry* 274, 26803-9 (1999).
36. Chien, S. Mechanotransduction and endothelial cell homeostasis: the wisdom of the cell. *American Journal of Physiology Heart and Circulatory Physiology* 292, H1209-24 (2007).
37. Seeley, R. R., Stephens, T. D. & Tate, P. *Anatomy and Physiology*. 1232 (McGraw-Hill: Boston, 2003).
38. Palmer, A. E. & Tsien, R. Y. Measuring calcium signaling using genetically targetable fluorescent indicators. *Nature Protocols* 1, 1057-65 (2006).
39. Bishara, N. B., Murphy, T. V. & Hill, M. A. Capacitative Ca(2+) entry in vascular endothelial cells is mediated via pathways sensitive to 2 aminoethoxydiphenyl borate and xestospongin C. *British Journal of Pharmacology* 135, 119-28 (2002).
40. Demer, L. L., Wortham, C. M., Dirksen, E. R. & Sanderson, M. J. Mechanical stimulation induces intercellular calcium signaling in bovine aortic endothelial cells. *The American Journal of Physiology* 264, H2094-102 (1993).
41. Quinto-Su, P. A., Lai, H. H., Yoon, H., Sims, C., Allbritton, N., & Venugopalan, V. Examination of laser microbeam cell lysis in a PDMS microfluidic channel using timeresolved imaging. *Lab on a Chip* 8, 408-14 (2008).
42. Seong, J., Lu, S. & Wang, Y. Live Cell Imaging of Src/FAK Signaling by FRET. *Cellular and Molecular Bioengineering* 4, 138-147 (2011).
43. Cherian, A. V. & Rau, K. R. Pulsed-laser-induced damage in rat corneas: time-resolved imaging of physical effects and acute biological response. *Journal of Biomedical Optics* 13, 024009 (2008).
44. Shergill, B., Meloty-Kapella, L., Musse, A. A., Weinmaster, G. & Botvinick, E. Optical tweezers studies on notch: single-molecule interaction strength is independent of ligand endocytosis. *Developmental Cell* 22, 1313-20 (2012).
45. Meloty-Kapella, L., Shergill, B., Kuon, J., Botvinick, E. & Weinmaster, G. Notch ligand endocytosis generates mechanical pulling force dependent on dynamin, epsins, and actin. *Developmental Cell* 22, 1299-312 (2012).
46. Neužil, P., Giselbrecht, S., Länge, K., Huang, T. J. & Manz, A. Revisiting lab-on-a-chip technology for drug discovery. *Nature Reviews Drug Discovery* 11, 620-32 (2012).
47. Young, E. W. K. & Simmons, C. A. Macro- and microscale fluid flow systems for endothelial cell biology. *Lab on a Chip* 10, 143-60 (2010).
48. Blackman, B. R., Garcia-Cardeña, G. & Gimbrone, M. A. A new in vitro model to evaluate differential responses of endothelial cells to simulated arterial shear stress waveforms. *Journal of Biomechanical Engineering* 124, 397-407 (2002).
49. Edelstein, A., Amodaj, N., Hoover, K., Vale, R. & Stuurman, N. Computer control of microscopes using µManager. *Current Protocols in Molecular Biology*, edited by Frederick M. Ausubel et al, Chapter 14, Unit 14.20 (2010).
50. Palmer, A. E. & Tsien, R. Y. Measuring calcium signaling using genetically targetable fluorescent indicators. *Nature Protocols* 1, 1057-65 (2006).
51. Park, J. W., Vahidi, B., Taylor, A. M., Rhee, S. W. & Jeon, N. L. Microfluidic culture platform for neuroscience research. *Nature Protocols* 1, 2128-36 (2006).
52. Yang, M. T., Fu, J., Wang, Y.-K., Desai, R. a & Chen, C. S. Assaying stem cell mechanobiology on microfabricated elastomeric substrates with geometrically modulated rigidity. *Nature Protocols* 6, 187-213 (2011).

53. U.S. Pat. No. 6,534,308, Method and apparatus for selectively targeting specific cells within a mixed cell population.
54. U.S. Pat. No. 6,642,018, Method for inducing a response in one or more targeted cells.
55. U.S. Pat. No. 7,092,557, Method and device for selectively targeting cells within a three-dimensional specimen.
56. U.S. Pat. No. 7,300,795, Optoinjection methods.
57. Rau K R, et al., Biophysical Journal, 91 (1): 317-329, 2006
58. Hellman A N, et al., Journal of Biophotonics, 2008.
59. A. Gulyani A biosensor generated via high-throughput screening quantifies cell edge Src dynamics,
60. C. Haug, Effect of diltiazem and verapamil on endothelin release by cultured human coronary smooth-muscle cells and endothelial cells
61. Vogel, A., J. Noack, K. Nahen, D. Theisen, S. Busch, U. Parlitz, D. X. Hammer, G. D. Noojin, B. A. Rockwell, and R. Birngruber. Energy balance of optical breakdown in water at nanosecond to femtosecond time scales. *Applied Physics B,* 68(2):271-280, 1999
62. Botvinick, E L and Wang, Y X. Methods in Cell Biology, (82): 497-523, 2007; Wang Y X, et. al., Nature, 434 (7036): 1040-1045, 2005
63. Wang Y X, et. al., Proceedings of the National Academy of Sciences, 104 (21): 8875-8879, 2007

What is claimed is:

1. A method for discovery and/or screening of test compounds that may modulate cellular mechanotransduction, the method comprising:
   providing at least one cellular sample;
   administering a test compound to the at least one cellular sample;
   initiating a microcavitation bubble before, during, or after the administering of the test compound, at a site within the at least one cellular sample;
   monitoring a signal related to the cellular mechanotransduction of the at least one cellular sample to which the test compound had been administered; and
   comparing the signal to a control signal, wherein a difference between the signal and the control signal indicates that the test compound modulates cellular mechanotransduction.

2. The method of claim 1, wherein initiating the microcavitation bubble comprises applying an energy source to the site.

3. The method of claim 2, wherein the energy source is selected from the group consisting of a laser, an ultrasonic transducer, a piezoelectric transducer, or combinations thereof.

4. The method of claim 1, wherein the at least one cellular sample comprises cells adherent to a two-dimensional substrate.

5. The method of claim 1, wherein the at least one cellular sample comprises a three-dimensional matrix.

6. The method of claim 5, wherein the three-dimensional matrix is selected from the group consisting of a hydrogel, a tissue, a reconstituted tissue, an extracellular matrix, a tissue scaffold or combinations thereof.

7. The method of claim 1, wherein the at least one cellular sample comprises a micro-patterned cellular sample configured to have some areas without cells.

8. The method of claim 1, wherein the microcavitation bubble is configured to form a microtsunami.

9. A method of testing a cellular response to a transient mechanical stimulus, the method comprising:
   providing a plurality of cellular samples;
   administering a test compound to at least a first cellular sample, and a control vehicle to at least a second cellular sample;
   initiating a microtsunami within at least the first and second cellular samples, wherein the test compound and control vehicle may be administered before, during, or after initiating the microtsunami;
   monitoring a signal related to the cellular response in at least the first and second cellular samples to which the test compound and the control vehicle had been respectively administered; and
   comparing the signals from at least the first and second cellular samples, wherein a difference between the signals indicates that the test compound modulates the cellular response to the transient mechanical stimulus.

10. A method for discovery and/or screening of test compounds that may modulate cellular mechanotransduction, the method comprising:
   providing a dish comprising a plurality of wells, each well comprising a cellular sample;
   administering a test compound to each of the cellular samples;
   initiating a microcavitation bubble before, during, or after the administering of the test compound, at a plurality of sites within the cellular samples;
   monitoring a plurality of signals related to the cellular mechanotransduction of the cellular samples to which the test compound had been administered; and
   comparing each signal to a control signal, wherein a difference between the signal and the control signal indicates that the test compound modulates cellular mechanotransduction for the corresponding cellular sample.

* * * * *